US012749567B2

(12) United States Patent
Neumann et al.

(10) Patent No.: US 12,749,567 B2
(45) Date of Patent: Sep. 29, 2026

(54) TECHNIQUE FOR IMAGE-TO-IMAGE TASK NEURAL NETWORK PRETRAINING

(71) Applicant: Siemens Healthineers AG, Forchheim (DE)

(72) Inventors: Dominik Neumann, Erlangen (DE); Alexandru Constantin Serban, Constanta (RO); Zhoubing Xu, Princeton, NJ (US); Bogdan Georgescu, Princeton, NJ (US); Florin-Cristian Ghesu, Baiersdorf (DE)

(73) Assignee: Siemens Healthineers AG, Forchheim (DE)

( * ) Notice: Subject to any disclaimer, the term of this patent is extended or adjusted under 35 U.S.C. 154(b) by 334 days.

(21) Appl. No.: 18/619,569

(22) Filed: Mar. 28, 2024

(65) Prior Publication Data

US 2024/0339199 A1 Oct. 10, 2024

(30) Foreign Application Priority Data

Apr. 5, 2023 (EP) .................................... 23166675

(51) Int. Cl.
*G16H 30/40* (2018.01)
*G06T 5/70* (2024.01)
(Continued)

(52) U.S. Cl.
CPC ............... *G16H 30/40* (2018.01); *G06T 5/70* (2024.01); *G06T 5/77* (2024.01); *G06T 7/11* (2017.01); *G06V 10/764* (2022.01); *G06T 2207/20081* (2013.01); *G06T 2207/20084* (2013.01); *G06T 2207/20132* (2013.01)

(58) Field of Classification Search
None
See application file for complete search history.

(56) References Cited

U.S. PATENT DOCUMENTS 10,528,812 B1 * 1/2020 Brouard ............... G06V 20/182
12,124,932 B1 * 10/2024 Poulis .................... G06N 20/00
(Continued)

OTHER PUBLICATIONS

Peng, Jialin, and Ye Wang. "Medical image segmentation with limited supervision: a review of deep network models." Ieee Access 9 (2021): 36827-36851. (Year: 2021).*
(Continued)

*Primary Examiner* — Samah A Beg

(57) ABSTRACT

A computer-implemented method for pretraining a downstream neural network for a novel image-to-image task to be performed on medical imaging data received from a medical scanner is provided. A database of augmented training data sets is generated based on a database of pre-existing training data sets. A set of at least two pretext neural network subsystems are jointly trained for performing (in particular partly self-supervised and partly weakly supervised) pretext tasks using the generated database. The downstream neural network is pretrained for the novel image-to-image task to be performed on medical imaging data received from a medical scanner. The pretraining is based on a subset of the modified weights of the pretext neural network subsystems, and/or on an output of a subset of layers of the set of pretext neural network subsystems.

20 Claims, 10 Drawing Sheets

(51) Int. Cl.

| | |
|---|---|
| ***G06T 5/77*** | (2024.01) |
| ***G06T 7/11*** | (2017.01) |
| ***G06V 10/764*** | (2022.01) |

(56) References Cited

U.S. PATENT DOCUMENTS

| | | | | |
|---|---|---|---|---|
| 2020/0184268 | A1* | 6/2020 | Lewis .................... | G06N 20/00 |
| 2022/0405933 | A1 | 12/2022 | Tajbakhsh et al. | |

OTHER PUBLICATIONS

Jing, Longlong, and Yingli Tian. "Self-supervised visual feature learning with deep neural networks: A survey." IEEE transactions on pattern analysis and machine intelligence 43.11 (2020): 4037-4058. (Year: 2020).*

Kebaili, Aghiles, Jérôme Lapuyade-Lahorgue, and Su Ruan. "Deep learning approaches for data augmentation in medical imaging: a review." Journal of imaging 9.4 (2023): 81. (Year: 2023).*

Tang et al., "Self-Supervised Pre-Training of Swin Transformers for 3D Medical Image Analysis", arXiv.2111.14791v2, 2022, pp. 1-16.

Taleb et al., "3D Self-Supervised Methods for Medical Imaging", arXiv:2006.03829v1, 2020, pp. 1-17.

Ghesu et al., "Self-Supervised Learning from 100 Million Medical Images", arXiv.2201.01283v1, 2022, pp. 1-13.

Haghighi et al., "DiRA: Discriminative, Restorative, and Adversarial Learning for Self-supervised Medical Image Analysis", IEEE/CVF Conference on Computer Vision and Pattern Recognition (CVPR), 2022, 17 pgs.

Crawshaw, "Multi-Task Learning with Deep Neural Networks: A Survey", arXiv:2009.09796v1, 2020, pp. 1-43.

Jeddi et al., "Tackling the Problem of Limited Data and Annotations in Semantic Segmentation", arXiv:2007.07357v1, 2020, pp. 1-10.

Zhang et al., "Dive into the details of self-supervised learning for medical image analysis", arXiv:2209.12157v2, 2023, pp. 1-29.

Extended European Search Report mailed Aug. 2, 2023 in connection with European Patent Application No. 23166675.1, 12 pgs.

Ronneberger et al., "U-Net: Convolutional Networks for Biomedical Image Segmentation", MICCAI, 2015, https://link.springer.com/chapter/10.1007/978-3-319-24574-4_28, 2015, pp. 234-241.

Shurrab et al., "Self-Supervised Learning Methods and Applications in Medical Imaging Analysis: A Survey", PeerJ Computer Science, 2022, pp. 1-51.

Qin et al., "Efficient Medical Image Segmentation Based on Knowledge Distillation", IEEE Transactions on Medical Imaging, 2020, pp. 1-12.

Hatamizadeh et al., "UNETR: Transformers for 3D Medical Image Segmentation", arXiv:21.03.10504v1, 2021, pp. 1-11.

U.S. Appl. No. 18/476,355, "Self-Supervised Training at Scale with Weakly-Supervised Latent Space Structure", filed Sep. 28, 2023.

European Patent Application No. 23465505.8, "Invariance Preserving Knowledge Distillation of Foundational Models for Medical Imaging Analysis", filed Mar. 15, 2023.

* cited by examiner

200

100

TECHNIQUE FOR IMAGE-TO-IMAGE TASK NEURAL NETWORK PRETRAINING

CROSS-REFERENCE TO RELATED APPLICATIONS

This application claims priority to European Patent Application No. 23166675.10, filed Apr. 5, 2023, the disclosure of which is herein incorporated by reference in its entirety.

BACKGROUND

State-of-the art artificial intelligence (AI)-based medical image analysis conventionally relies on deep-learning (DL) to train neural networks for tasks such as image segmentation, classification, or clinical outcome prediction. It is well known that the performance of such models is conventionally strongly correlated with the amount of high-quality curated and annotated training data, especially when using standard supervised learning methods. However, conventional proper data annotation is quite costly and time-consuming, especially in the medical domain.

For several years, self-supervised learning (SSL) methods have been gaining traction in the computer vision community, and recently also in medical imaging, see e.g., [1]. SSL methods are designed to reduce the need for high quality annotations relying instead on so-called pretext tasks [2] to exploit unlabeled data, i.e., tasks that are designed in a way that if the network can solve them, it will also inherently learn features that are useful for the “real” tasks (also denoted as downstream tasks). It has been shown that pretraining using SSL can provide a multitude of benefits to downstream tasks, including increased accuracy, better training stability, and faster training convergence [3].

The optimal set of SSL pretext tasks that benefit certain types of downstream tasks is task-dependent. Hence, blindly re-using tasks proven successful in processing of “natural” images (e.g., photos), or other computer vision domains may not yield optimal results in medical imaging. Furthermore, it is not straightforward to extend standard self-supervised pretraining methods to include prior knowledge or existing annotations on a subset of the available data (e.g., from previous projects), which might have the potential to provide additional benefits at no additional cost. Finally, most SSL frameworks focus on SSL-only pretraining, and an extension towards including additional loss signals from standard learning tasks (e.g., supervised segmentation) is not straightforward.

The standard approach for training AI models in the medical domain has been, for many years, supervised learning. Recently, the concept of pretraining (e.g., using SSL) on a large data set plus finetuning on a downstream task has started to become more popular [1,3]. However, it is still a field of active research with many questions unanswered, such as: What is the optimal set of pretext tasks? How can one leverage both SSL and prior knowledge and/or conventional learning? What are the differences in standard computer vision tasks versus medical imaging?

While Haghighi et al. [4] address the questions of the best pretext task and, to some extent, the differences between standard computer vision versus medical imaging, it remains an open question how to efficiently optimize the analysis of medical images, in particular for image-to-image tasks.

BRIEF SUMMARY OF THE INVENTION

It is therefore an object of the present invention to provide a solution for efficiently (in particular in terms of time, amount of manually annotated training data sets) training a (e.g., downstream) neural network (NN) for performing a (in particular novel) image-to-image task. Alternatively or in addition, it is object of the present invention to increase accuracy, training stability, and/or training convergence of a (e.g., downstream) neural network (NN) for performing a (in particular novel) image-to-image task. Further alternatively or in addition, it is an object of the present invention to exploit the power of self-supervised learning (SSL) while (e.g., simultaneously) making use of the benefits of (e.g., at least weakly) supervised learning.

This object is solved by a method for pretraining a downstream neural network (NN) for a novel image-to-image task to be performed on medical imaging data received from a medical scanner, by a computing device, by a system, by a computer program (and/or a computer program product), and by a computer-readable storage medium according to the appended independent claims. Advantageous aspects, features and embodiments are described in the dependent claims and in the following description together with advantages.

In the following, the solution according to the invention is described with respect to the claimed method for pretraining a downstream NN for a novel image-to-image task to be performed on medical imaging data received from a medical scanner as well as with respect to the claimed computing device. Features, advantages, or alternative embodiments herein can be assigned to the other claimed objects (e.g., the system, the computer program or a computer program product), and vice versa. In other words, claims for the computing device for pretraining a downstream NN for a novel image-to-image task to be performed on medical imaging data received from a medical scanner, and/or for the system, can be improved with features described or claimed in the context of the method. In this case, the functional features of the method are embodied by structural units of the system and vice versa, respectively.

As to a method aspect, a (in particular computer-implemented) method for pretraining a downstream neural network (NN) for a novel image-to-image task to be performed on medical imaging data received from a medical scanner is provided.

The method comprises a step of generating a database of augmented training data sets based on at least one database of pre-existing training data sets. Generating an augmented training data set for the database of augmented training data sets from an existing training data set comprises a substep of creating a mask (also denoted as label, and/or annotation) in relation to each of a set of existing trained image-to-image models by applying each existing trained image-to-image model within the set to a pre-existing training data set within the at least one database of pre-existing training data sets. Each existing trained image-to-image model within the set of existing trained image-to-image models is trained for creating a mask in relation to a medical imaging data set comprised in at least one of the pre-existing training data sets. Generating the augmented training data set for the database from the existing training data set further comprises a substep of aggregating the created masks for the pre-existing training data set into a multi-mask. Generating the augmented training data set for the database from the existing training data set still further comprises a substep of assembling the augmented training data set. The augmented training data set comprises the multi-mask and the medical imaging data set from the pre-existing training data set.

The method further comprises a step of (in particular jointly) training a set of pretext NN subsystems (e.g., jointly forming a pretext NN system) for performing pretext tasks using the generated database of augmented training data sets. The set of pretext NN subsystems comprises at least two different pretext NN subsystems. The training of the set of pretext NN subsystems comprises a substep of selecting an augmented training data set from the generated database. The training of the set of pretext NN subsystems further comprises a substep of cropping a patch from the selected augmented training data set. The cropping comprises cropping the medical imaging data set and the aggregated multi-mask of the augmented training data set at the same voxel location and/or pixel location for the multi-mask and the medical imaging data set. The training of the set of pretext NN subsystems further comprises a substep of generating a set of transformed patches. The generating of the set of transformed patches comprises performing at least one predetermined transformation operation on the cropped patch. The training of the set of pretext NN subsystems further comprises a substep of performing the pretext tasks using the set of pretext NN subsystems. One or more generated transformed patches are used as input for each pretext NN subsystem. Any one, or each, pretext task comprises classifying, and/or applying an inverse of, the at least one predetermined image-to-image transformation operation. The training further comprises determining a pretext NN subsystem-specific loss function. The pretext NN subsystem-specific loss function is indicative of a similarity between the output of the pretext NN subsystem and a mask within the aggregated multi-mask, and/or a similarity between the output of the pretext NN subsystem and medical imaging data comprised in the cropped patch. The at least two different pretext NN subsystems differ in the type of output. The type of output comprises a mask according to one of the masks within the aggregated multi-mask. Alternatively or in addition, the type of output comprises a classification of the predetermined image-to-image transformation operation. Further alternatively or in addition, the type of output comprises a reconstructed version of the (e.g., original, and/or cropped) medical imaging data. The training of the set of pretext NN subsystems still further comprises a substep of modifying (e.g., optimizing) each pretext NN subsystem within the set of pretext NN subsystems based on a predetermined combination of the task-specific loss functions of the at least two different pretext NN subsystems. The modifying comprises modifying (e.g., optimizing) one or more weights of the pretext NN subsystem.

The method still further comprises a step of pretraining the downstream NN for the novel image-to-image task to be performed on medical imaging data received from a medical scanner, wherein the pretraining is based on (e.g., at least) a subset of the modified weights of the pretext NN subsystems, and/or is based on an output of (e.g., at least) a subset of layers (e.g., the output layer of the encoder and/or of the decoder of a pretext NN subsystem) of the set of pretext NN subsystems.

By the inventive technique, self-supervised learning (SSL) of a subset of the pretext NN subsystems may be combined with prior knowledge of the existing trained image-to-image models, e.g., in terms of a weakly supervised learning of a further subset of the pretext NN subsystems, for which the multi-mask of the augmented training data set comprises the pseudo ground truth (also denoted as weak ground truth). The pseudo ground truth may correspond to, or may closely resemble, the ground truth. Alternatively or in addition, the ground truth may be supervised, verified, and/or issued, by an expert (e.g., a medical practitioner). Further alternatively or in addition, the pseudo ground truth may be (e.g., solely) computer (and/or automatically) generated (in particular without human supervision), and/or e.g., solely) generated by an existing trained image-to-image model.

The inventive technique can in particular be applied to training a NN for a segmentation, and/or a classification, task of an anatomical structure, organ, and/or abnormality, for which no existing trained image-to-image model is available (and/or known) as the image-to-image task. The use of the inventive technique can improve a training stability, robustness, training convergence, timescale required for the training, and/or performance of the downstream NN. Thereby, an accuracy and timeline of a medical evaluation based on the medical imaging data received from the medical can be improved, which may result in an improved patient outcome.

The inventive technique can be applied to any real-time application that can be formulated as an image-to-image task. E.g., a real-time application may comprise tracking and/or optical guidance for surgery, e.g., detecting the location of the tip of a catheter inserted into the patient and tracking it in real-time. The detecting of the tip of the catheter may be formulated as an image-to-image task, where the input comprises medical imaging data, and the output comprises a "probability map" that indicates the likely position of the catheter tip. Alternatively or in addition, applying the inventive technique to a real-time application relies on real-time medical imaging data being available, e.g., comprising fluoroscopy, and/or 2D ultrasound, medical imaging data for 2D imaging-based applications.

By the inventive technique, a need for a large number of training data sets with high-quality manual annotations, and/or masks, for the training of the downstream NN may be reduced. Alternatively or in addition, the training of the downstream NN may be performed more efficiently.

An image-to-image task and/or model has an image as input and provides a (different or transformed) image as output.

Any medical image data set may briefly be denoted as medical image data, medical image, and/or image (e.g., in a volumetric, and/or three-dimensional, 3D, context). Alternatively or in addition, in a two-dimensional (2D) context, a medical image (and/or briefly image) may refer to a plane (and/or surface) within a 3D medical image data set.

Each of the existing trained image-to-image models may be trained on a (e.g., exactly one) database of pre-existing training data sets. E.g., an existing trained image-to-image model may have been trained on pre-existing training data sets, which each comprise a magnetic resonance imaging (MRI) medical imaging data set comprising a patient's heart with a manually performed segmentation of the heart as (e.g., ground truth) mask, for performing segmentations of the heart in further MRI medical imaging data sets.

The existing trained image-to-image models may comprise artificial intelligence (AI) models, NNs, deep learning (DL) and/or reinforcement learning (RL) models with arbitrary architecture. Alternatively or in addition, the existing trained image-to-image models used for generating the database of augmented training data sets may be selected (e.g., solely) based on the type of medical imaging data they use as input, and/or the type of mask they produce as output.

Preferably, the image-to-image model(s) have been trained with training data, stored in the database or parts thereof.

The set of pretext NN subsystems may be comprised in a (e.g., overall, superordinate, and/or overarching) pretext NN system. Two or more pretext NN subsystems within the set of pretext NN subsystems may share parts of the pretext NN system architecture. E.g., two or more pretext NN subsystems may share an (e.g., image, and/or mask) encoder, a (e.g., image, and/or mask) decoder, and/or a projection head.

The set of pretext NN subsystems may comprise at least a part of a NN architecture that is similar, and/or related, to the architecture of the downstream NN. E.g., the set of pretext NN subsystems and the downstream NN may each comprise at least one image encoder, and/or at least one mask decoder.

An architecture of any one of the set of pretext NN subsystems, and/or of the downstream NN, may comprise an encoder-decoder based architecture, and/or a transformer-based architecture.

Alternatively or in addition, the pretext NN subsystems need not be (e.g., really) separate entities, but may rather are share a large portion of the pretext NN system (e.g., the same instance of the encoder may be used across different pretext tasks, meaning that the data to compute the loss of each pretext task goes through the same NN components and thus the different pretext losses jointly optimize the weights of those shared NN components).

Alternatively or in addition, the loss functions (e.g., minimizing a loss) may be a means to optimizing the pretext NN system. Further alternatively or in addition, any one of the pretext NN subsystems, and/or the weights of any one of the pretext NN subsystems may be optimized with respect to a predetermined combination of the task-specific loss functions.

Any one of the existing trained image-to-image models may comprise a machine learning (ML) model, and/or an artificial intelligence (AI) based model, such as a NN, a deep learning (DL), and/or reinforcement learning (RL) model.

The pre-existing training data sets may be stored in the database and/or may also be denoted as in stock, available, existing, and/or existent training data sets. Each pre-existing training data set may comprise a medical imaging data set. Optionally, any one of the pre-existing training data sets may comprise a mask.

A database of pre-existing training data sets may comprise medical imaging data sets received by a predetermined medical imaging modality (e.g., CT, and/or MRI).

Alternatively or in addition, a database of pre-existing training data sets may comprise medical imaging data sets comprising a predetermined anatomical structure, a predetermined organ, and/or a predetermined abnormality (e.g., a lesion, and/or a tumor, in particular relative to a predetermined anatomical structure and/or a predetermined organ).

The one or more databases of pre-existing training data sets, from which the database of augmented training data sets is generated, may be selected based on a spatial, and/or functional, proximity of anatomical structures, and/or organs, captured in the medical imaging data sets comprised in the (pre-existing, and/or augmented) training data sets with the novel image-to-image task to be performed, by the downstream NN, on medical imaging data received from a medical scanner. E.g., if the novel image-to-image task comprises generating a mask (e.g., comprising a segmentation, and/or classification) of the esophagus, the selected (and/or applied) existing trained image-to-image models may comprise generating a mask (in particular the same type of mask) for any organ, and/or any anatomical structure, of the (e.g., upper) torso. Alternatively or in addition, a downstream NN may be pretrained for an image-to-image task applied to one type of (e.g., hip, and/or knee) joint by using one or more databases of pre-existing training data comprising any other type of (e.g., hip, knee, ankle, wrist, and/or arm) joint.

The mask may also be denoted as annotation, training label and/or (e.g., pseudo) ground truth. Alternatively or in addition, the mask may comprise a label, and/or a bitmap, per voxel and/or pixel of the corresponding medical imaging data set. Further alternatively or in addition, the medical imaging data set may be represented by one or more (e.g., further) bitmaps per voxel and/or pixel, e.g., comprising a red green blue alpha (RGBA) coding per voxel, and/or pixel.

The mask may in particular comprise a segmentation, and/or a classification.

The multi-mask may also be denoted as multiple annotations, multi-mask mask, and/or multi-mask (e.g., pseudo) ground truth. The multi-mask may comprise one or more unsupervised (also: AI generated) masks.

The at least one pre-existing database of medical imaging data may comprise medical imaging data obtained (also: received) from a medical scanner using a predetermined imaging modality.

The (e.g., predetermined) imaging modality may comprise magnetic resonance imaging (MRI), computed tomography (CT), ultrasound (US), positron emission tomography (PET), single photon emission computed tomography (SPECT), and/or radiography (also denoted as X-ray imaging).

Alternatively or in addition, the at least one pre-existing database of medical imaging data sets may comprise medical imaging data sets of a predetermined dimensionality, in particular two-dimensional (2D) data, and/or three-dimensional (3D) data (also denoted as volumetric data). E.g., 3D data received from a CT scanner may be converted to resemble 3D data received from an MRI scanner, and the at least one pre-existing database may comprise converted CT data as well as MRI data.

The predetermined transformation operation, which may be applied to the cropped patch, may comprise (e.g., discrete) rotations of the cropped patch, flips across a plane withing the cropped patch, adding noise, and/or removing and/or obfuscating a region of the medical imaging data set.

According to some embodiments, the medical imaging data sets may comprise a temporal sequence of medical imaging data, and/or a spatial sequence of slices. The predetermined transformation operation may comprise shuffling (also: scrambling) the medical imaging data of the temporal sequence, and/or the slices of the spatial sequence. Alternatively or in addition, the predetermined transformation operation may comprise shuffling (also: scrambling) cropped patches within a medical imaging data set.

Any predetermined transformation operation may be applied (e.g., simultaneously, and/or equally) to the medical imaging data set and the associated multi-mask.

A subset of the pretext NN subsystems may (e.g., only) perform the one or more predetermined transformation operation. Alternatively or in addition, a (e.g., different) subset of the pretext NN subsystems may perform an image-to-image task, in particular a segmentation and/or classification, e.g., akin (and/or of the same type, in particular segmentation and/or classification) to the image-to-image task of the downstream NN.

Alternatively or in addition, a subset of the pretext NN subsystems may comprise, e.g., a (in particular not image-to image) classification task, and/or a reconstruction task. E.g., a rotation task may comprise, or may be set up, as a classification task. An image patch may be input into an (e.g., image) encoder of a pretext NN subsystem and forwarded to a classification head. The output of the classification head may comprise a probability for each predefined class. The pre-defined classes may correspond to the predefined sets of possible rotations. E.g., in a simple embodiment four possible rotations {"90° along x-axis", "90° along y-axis", "90° along z-axis", "no rotation"} may be defined. The pretext NN subsystem may be tasked to predict a high probability for one rotation operation that was in fact applied to that patch, and low probabilities for the others.

Alternatively or in addition, classifying the (e.g., at least one) predetermined image-to-image transformation operation may comprise assigning probabilities to a (in particular discrete) set of (e.g., predetermined) image-to-image transformation operation. Further alternatively or in addition, any one, or each, pretext task may comprise applying an inverse predetermined image-to-image transformation operation.

The modifying of each pretext NN subsystem may be iterative. E.g., the steps of selecting an augmented training data set, cropping and generating transformed patches and performing the set of pretext NN subsystems may be repeated (e.g., multiple times) with modified weights until the predetermined combination (e.g., weighted sum) of the task-specific loss functions remains (at least approximately) constant.

The downstream NN may also be denoted as operational NN. Alternatively or in addition, the downstream NN may be subject to supervised training.

In an embodiment, pretraining the downstream NN may comprise an initialization of the downstream NN with some weights, which are based on some weights of the (e.g., modified) pretext NN subsystems. This embodiment may, e.g., be applied to a downstream NN for performing a novel medical image segmentation task.

Initializing the downstream NN with at least a subset of the modified (also: pretrained) weights of the pretext NN subsystems may comprise selecting weights, e.g., for predetermined layers of the downstream NN. E.g., at subset of weights of an image encoder, and/or of a mask decoder, of the downstream NN may be initialized based on the modified (also: pretrained) weights of the corresponding pretext NN subsystems.

In another embodiment, which may be combined with the preceding embodiment, the pretext NN system comprising the set of pretext NN subsystems, and/or any one of the pretext NN subsystems, may be large (e.g., in terms of computing, processor, memory, and/or hardware resources) compared to the downstream NN. E.g., significantly less computing resources may be available during application of the downstream NN as compared to the pretraining, and/or training, of the downstream NN.

Knowledge distillation may comprise, and/or may denote, extracting knowledge from a large NN (e.g., the pretext NN system, and/or the set of pretext NN subsystems) and transferring it to a smaller NN (e.g., the downstream NN), such that the output of the smaller NN resembles the output of the large NN up to some degree. The large NN may conventionally be called the "teacher" and the small NN the "student". If for instance, the training of the set of pretext NN systems produces a very powerful, but large encoder, a teacher-student approach may be employed to extract the most relevant portions of the "teacher encoder" into the "student encoder" (e.g., as the encoder for the downstream NN). Examples are e.g., provided by Dian Qin et al. [8], which is incorporated herein by reference.

The method may further comprise a step of selecting the set of existing trained image-to-image models for the step of generating the database of augmented training data sets. Alternatively or in addition, the method may further comprise a step of receiving, from the at least one database, the pre-existing training data sets for the step of generating the database of augmented training data sets.

The selection of the set of existing trained image-to-image models may be specific to the novel image-to-image task to be performed on medical imaging data by the downstream NN.

The method may further comprise a step of training the downstream NN by initializing weights of the downstream NN based on the subset of the modified weights of the pretext NN subsystems.

Alternatively or in addition, the training of the downstream NN may comprise a pretraining, in which the downstream NN is pretrained to reproduce the output of the subset of the layers of the set of pretext NN subsystems. The output of the subset of the layers of the set of pretext NN subsystems may, e.g., comprise a feature map as the output of an (e.g., image) encoder, a segmentation, and/or classification, as the output of a (e.g., mask) decoder, and/or a selection of a region of interest (ROI).

The training of the downstream NN may be performed using a training database of medical imaging data in relation to the novel image-to-image task to be performed by the downstream NN. Alternatively or in addition, the method may further comprise a step of applying the trained downstream NN to an, in particular current, medical imaging data set received from a medical scanner.

The training database of the downstream NN may comprise synthetic medical imaging data, and/or real medical imaging data previously received from a medical scanner.

The at least one transformation operation in the step of generating the set of transformed patches may comprise a rotation, in particular by a discrete angle, and more particularly by an integer multiple of 90° along a symmetry axis of the cropped patch. Alternatively or in addition, the at least one transformation operation in the step of generating the set of transformed patches may comprise a flip across an image plane. Alternatively or in addition, the at least one transformation operation in the step of generating the set of transformed patches may comprise a masking of one or more voxels, and/or pixels, of the cropped patch with noise. Alternatively or in addition, the at least one transformation operation in the step of generating the set of transformed patches may comprise changing an intensity of one or more voxels, and/or pixels, of the medical imaging data of the cropped patch.

Alternatively or in addition, the at least one transformation operation in the step of generating the set of transformed patches may comprise inpainting the cropped patch. The inpainting may comprise removing, and/or obfuscating, a region of the image, and/or of any one of the masks of the multi-mask, of the cropped patch. Alternatively or in addition, the at least one transformation operation in the step of generating the set of transformed patches may comprise shuffling subpatches of the cropped patch. The shuffling may comprise permuting spatial positions of the subpatches. Further alternatively or in addition, the at least one transformation operation in the step of generating the set of transformed patches may comprise, in case the medical imaging data comprise a temporal sequence of data, a shuffling of temporal instances of the cropped patch. The shuffling of temporal instances may comprise permuting temporal assignments of the instances.

The changing of the intensity of one of more voxels, and/or pixels, may (e.g., only) be performed on the medical imaging data. Alternatively or in addition, any one of the transformation operations (e.g., with exception of changing the intensity) may be performed simultaneously on the medical imaging data and the multi-mask.

The transformation operations may be combined. E.g., a rotation, and/or flip, may be followed by a masking of one or more voxels, and/or pixels.

The image-to-image task of the downstream NN may comprise, and/or correspond to, a segmentation of one or more predetermined anatomical structures comprised in a medical imaging data set received from a medical scanner. Alternatively or in addition, the image-to-image task of the downstream NN may comprise, and/or correspond to, a classification of one or more predetermined anatomical structures comprised in the medical imaging data set received from the medical scanner.

The image-to-image task of the downstream NN may, e.g., comprise a segmentation of the esophagus, liver, multi ribs, spinal canal, a bronchus, and/or a femur head (also: femoral head) imaged (and/or comprised in the medical imaging data) by the medical scanner.

The training of the pretext NN subsystems may use self-supervised learning (SSL) and/or weak supervised learning.

A subset of the pretext NN subsystems, in particular only comprising classifying, and/or applying inverse, (e.g., discrete) transformation operations, may be trained using SSL. Alternatively or in addition, a (e.g., different) subset of the pretext NN subsystems, in particular comprising a segmentation and/or classification, may be trained using weakly supervised learning.

Weakly supervised learning (also denoted as weakly supervised training; briefly also: weak supervision) may comprise making use of a mask, in particular created by one of the existing trained image-to-image models. E.g., a pretext NN subsystem may be trained with weak supervision if its output is a mask, and the pretext NN subsystem-specific loss function makes use of one of the masks within the multi-mask of an augmented training data set.

Weakly supervised learning may refer to training any NN (e.g., any one of the pretext NN subsystems) using a (e.g., automatically, and/or without human input) computer-generated mask (and/or pseudo ground truth). Alternatively or in addition, supervised learning may refer to training any NN (e.g., the downstream NN) using a manually (and/or with human input) generated mask (and/or ground truth).

Alternatively or in addition, "weak supervision" (e.g., as opposed to just "supervision") may denote that there is no (e.g., true) ground truth mask used. Instead, automatically generated masks (and/or pseudo ground truths) from existing trained image-to-image models, which are not verified by any expert (e.g., medical practitioner) in any way, may be used. Alternatively or in addition, according to the inventive technique, the existing trained image-to-image models may be simply "trusted" to generate meaningful output, hence "weak supervision" (e.g., when applying the pseudo ground truth for training one or more pretext NN subsystems).

The training of the downstream NN may comprise supervised learning. The supervised learning may comprise using training data sets comprising medical imaging data with (in particular manually, and/or by an expert, created) masks (and/or ground truths).

The set of pretext NN subsystems may comprise an image-to-image task that corresponds to, and/or comprises, a segmentation of one or more anatomical structures comprised in the cropped patch. Alternatively or in addition, the set of pretext NN subsystems may comprise an image-to-image task that corresponds to, and/or comprises, a classification of the one or more anatomical structures (and/or organs, and/or abnormalities) comprised in the cropped patch. Alternatively or in addition, the set of pretext NN subsystems may comprise an image-to-image task that corresponds to, and/or comprises, a masking of the one or more anatomical structures comprised in the cropped patch. Alternatively or in addition, the set of pretext NN subsystems may comprise an image-to-image task that corresponds to, and/or comprises, a denoising of the cropped patch. Alternatively or in addition, the set of pretext NN subsystems may comprise an image-to-image task that corresponds to, and/or comprises, a rotation classification, and/or rotation recovery, of the cropped patch. Alternatively or in addition, the set of pretext NN subsystems may comprise an image-to-image task that corresponds to, and/or comprises, a flip classification, and/or flip recovery, along an image plane within the cropped patch. Further alternatively or in addition, the set of pretext NN subsystems may comprise an image-to-image task that corresponds to, and/or comprises, a contrastive task. The contrastive task may comprise identifying a positive pair in case of overlapping patches, and/or a negative pair in case of non-overlapping patches.

The overlapping patches may comprise patches originating from the same cropping with independently performed predetermined transformation operations.

The anatomical structure may comprise an organ, and/or an abnormality (e.g., a lesion, and/or a tumor).

The contrastive task may be performed by a projection head. Alternatively or in addition, the rotation classification, and/or the rotation recovery, may be performed by a classification head. Alternatively or in addition, the flip classification, and/or the flip recovery, may be performed by a classification head. Further alternatively or in addition, the denoising, masking, classification (e.g., of anatomical structures, organs, and/or abnormalities), and/or segmentation may be performed by a decoder.

The task-specific loss may comprise a cross entropy loss (e.g., for the rotation classification, rotation recovery, flip classification, and/or flip recovery), a DICE loss (e.g., for the masking, classification of anatomical structure, organs, and/or abnormalities, and/or segmentation), an L1 loss (e.g., for the denoising), and/or a contrastive loss (e.g., for the contrastive task).

The denoising may also be denoted as reconstruction task (briefly: reconstruction).

A NN architecture of any one of the pretext NN subsystems, and/or the downstream NN, may comprise at least one encoder, and/or at least one decoder.

Initializing the weights for the training of the downstream NN based on (e.g., at least) a subset of the modified weights (also denoted as pretrained weights) of the pretext NN subsystems may comprise using the pretrained weights of (at least a predetermined subset of layers) of the (in particular image) encoder of a pretext NN subsystem for the downstream NN.

Alternatively or in addition, initializing the weights for the training of the downstream NN based on (e.g., at least) a subset of the modified weights (and/or pretrained weights) of the pretext NN subsystems may comprise using the pretrained weights of (at least a predetermined subset of layers) of the (in particular mask) decoder of a pretext NN subsystem for the downstream NN.

Further alternatively or in addition, initializing the weights for the training of the downstream NN based on (e.g., at least) a subset of the modified weights (and/or pretrained weights) of the pretext NN subsystems may comprise using a reduced number of parameters, and/or a reduced number of layers, of the (in particular image) encoder, and/or (in particular mask) decoder, of a pretext NN subsystem for the downstream NN.

The medical imaging data set may comprise a two-dimensional (2D) image data set. Alternatively or in addition, the medical imaging data set may comprise a three-dimensional (3D) image data set.

The 3D image data set may also be denoted as volumetric data set.

The medical imaging data set of any augmented training data set in the database may be received from a predetermined medical imaging modality. Optionally the medical imaging modality is selected from the group of CT, MRI, US, PET, SPECT, and/or radiography. Radiography may also denoted as X-ray scanning.

One patch may be cropped per augmented training data set per training epoch in an embodiment. In a further embodiment, two or more, in particular non-overlapping, patches may be cropped per augmented training data set per training epoch.

A NN architecture of any one of the pretext NN subsystems, and/or the downstream NN, may comprise a convolutional, in particular U-Net, architecture, a transformer architecture, and/or a combination of a convolutional, in particular U-net, and transformer architecture.

A convolutional NN (CNN) may comprise hidden layers performing convolutions, e.g., converting an image into a feature map.

A U-Net may comprise a fully-connected CNN with additional connections between non-neighboring layers, in particular between downconverting and upconverting layers (e.g., between encoder layers and decoder layers).

A transformer may comprise a NN comprising self-attention layers.

A variant of a U-Net may be called "UNETR", e.g., described A. Hatamizadeh in [9], which is included herein by reference. The UETR may combine a CNN and transformer within a U-Net-type of architecture by relying on a transformer as the encoder and a CNN as the decoder. Some further modifications to original U-Net architecture may be performed, in particular regarding skip connections between the transformer as encoder and the conventional, and/or CNN, decoder.

As to a device aspect, a computing device for pretraining a downstream NN for a novel image-to-image task to be performed on medical imaging data received from a medical scanner is provided.

The computing device comprises a database generating module configured for generating a database of augmented training data sets based on at least one database of pre-existing training data sets. The database generating module comprises a mask creating sub-module configured for creating a mask in relation to each of a set of existing trained image-to-image models by applying each existing trained image-to-image model within the set to a pre-existing training data set within the at least one database of pre-existing training data sets. Each existing trained image-to-image model within the set of existing trained image-to-image models is trained for creating a mask in relation to a medical imaging data set comprised in at least one of the pre-existing training data sets. The database generating module further comprises an aggregating sub-module configured for aggregating the created masks for the pre-existing training data set into a multi-mask. The database generating module still further comprises an assembling sub-module configured for assembling the augmented training data set. The augmented training data set comprises the multi-mask and the medical imaging data set from the pre-existing training data set.

The computing device further comprises a pretext task training module configured for (in particular jointly) training a set of pretext NN subsystems for performing pretext tasks using the generated database of augmented training data sets. The set of pretext NN subsystems comprises at least two different pretext NN subsystems. The pretext task training module comprises an augmented training data set selecting sub-module configured for selecting an augmented training data set from the generated database. The pretext task training module further comprises a patch cropping sub-module configured for cropping a patch from the selected augmented training data set. The cropping comprises cropping the medical imaging data set and the aggregated multi-mask of the augmented training data set at the same voxel location, and/or pixel location, for the multi-mask and the medical imaging data set. The pretext task training module further comprises a transformed patches generating module configured for generating a set of transformed patches. The generating of the set of transformed patches comprises performing at least one predetermined transformation operation on the cropped patch. The pretext task training module further comprises a set of pretext NN subsystems configured for performing the pretext tasks. One or more generated transformed patches are used as input for each pretext NN subsystem. Any one, or each, pretext task comprises classifying, and/or applying an inverse of, the at least one predetermined image-to-image transformation operation. The training further comprises determining a pretext NN subsystem-specific loss function. The pretext NN subsystem-specific loss function is indicative of a similarity between the output of the pretext NN subsystem and a mask within the aggregated multi-mask, and/or a similarity between the output of the pretext NN subsystem and medical imaging data comprised in the cropped patch. The at least two different pretext NN subsystems differ in the type of output. The type of output comprises a mask according to one of the masks within the aggregated multi-mask. Alternatively or in addition, the type of output comprises a classification of the predetermined image-to-image transformation operation. Further alternatively or in addition, the type of output comprises a reconstructed version of the (e.g., original, and/or cropped) medical imaging data. The pretext task training module still further comprises a pretext NN subsystem modifying sub-module configured for modifying (e.g., optimizing) each pretext NN subsystem within the set of pretext NN subsystems based on a predetermined combination of the task-specific loss functions of the at least two different pretext NN subsystems. The modifying comprises modifying (e.g., optimizing) one or more weights of the pretext NN subsystem.

The computing device still further comprises a downstream NN pretraining module configured for pretraining the downstream NN for the novel image-to-image task to be performed on medical imaging data received from a medical scanner. The pretraining of the downstream NN may be based on (e.g., at least) a subset of the modified weights of the pretext NN subsystems. Alternatively or in addition, the pretraining of the downstream NN may be based on an output of (e.g., at least) a subset of layers (e.g., the output layer of the encoder and/or of the decoder of a pretext NN subsystem) of the set of pretext NN subsystems.

The computing device may be configured to perform the method according to the method aspect. Alternatively or in addition, the computing device may comprise any feature disclosed in the context of the method aspect.

As to a system aspect, a system for pretraining a downstream NN for a novel image-to-image task to be performed on medical imaging data received from a medical scanner is provided. The system comprises a computing device according to the device aspect. The system further comprises a downstream NN, which is configured for being pretrained by the downstream NN pretraining module of the computing device.

Optionally, the system further comprises a memory for storing the database of augmented training data sets.

Alternatively or in addition to comprising the computing device, the system may comprise modules, sub-modules, and/or interfaces, with functionalities corresponding to the functionalities disclosed in the context of the computing device. The modules, sub-modules, and/or interfaces of the system may in particular be distributed over multiple hardware units.

The system may be configured to perform the method according to the method aspect. Alternatively or in addition, the system may comprise any feature disclosed in the context of the method aspect.

As to a further aspect, a computer program (and/or computer program product) comprising program elements which induce a computing device to carry out the steps of the method for pretraining a downstream NN for a novel image-to-image task to be performed on medical imaging data received from a medical scanner according to the method aspect is provided. The steps are carried out when the program elements are loaded into a memory of the computing device.

As to a still further aspect, a computer-readable medium on which program elements are stored that can be read and executed by a computing device is provided, in order to perform steps of the method for pretraining a downstream NN for a novel image-to-image task to be performed on medical imaging data received from a medical scanner according to the preceding method aspect. The method steps are performed when the program elements are executed by the computing device.

The properties, features, and advantages of this invention described above, as well as the manner they are achieved, become clearer and more understandable in the light of the following description and embodiments, which will be described in more detail in the context of the drawings. This following description does not limit the invention on the contained embodiments. Same components or parts can be labeled with the same reference signs in different figures. In general, the figures are not for scale.

It shall be understood that a preferred embodiment of the present invention can also be any combination of the dependent claims or (e.g., above) embodiments with the respective independent claim.

These and other aspects of the invention will be apparent from and elucidated with reference to the embodiments described hereinafter.

Any reference signs in the claims should not be construed as limiting the scope.

DETAILED DESCRIPTION

Figure 1:
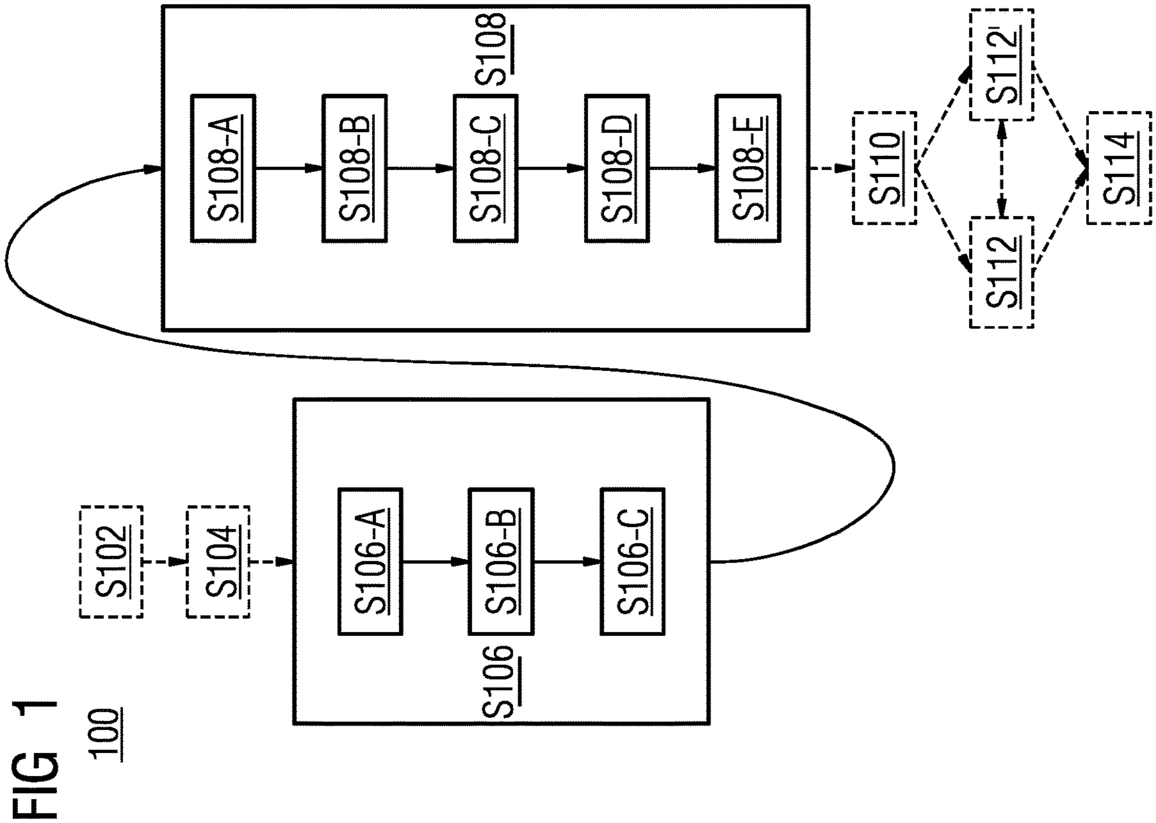
FIG. 1 is a flow chart of a method for pretraining a downstream neural network (NN) for a novel image-to-image task to be performed on medical imaging data received from a medical scanner according to a preferred embodiment of the present invention.

FIG. 1 schematically illustrates an example of a (in particular computer-implemented) method for pretraining a downstream neural network (NN) for a novel image-to-image task to be performed on medical imaging data received from a medical scanner. The method is generally referred to by reference sign 100.

The method 100 comprises a step S106 of generating a database of augmented training data sets based on at least one database of pre-existing training data sets. Generating S106 an augmented training data set for the database from an existing training data set comprises a sub-step S106-A of creating a mask in relation to each of a set of existing trained image-to-image models by applying each existing trained image-to-image model within the set to a pre-existing training data set within the at least one database of pre-existing training data sets. Each existing trained image-to-image model within the set of existing trained image-to-image models is trained for creating a mask in relation to a medical imaging data set comprised in at least one of the pre-existing training data sets. Generating S106 an augmented training data set for the database from an existing training data set further comprises a sub-step S106-B of aggregating the created S106-A masks for the pre-existing training data set into a multi-mask. Generating S106 an augmented training data set for the database from an existing training data set further comprises a sub-step S106-C of assembling the augmented training data set. The augmented training data set comprises the (e.g., aggregated S106-B) multi-mask and the medical imaging data set from the pre-existing training data set.

The method 100 further comprises a step S108 of (in particular jointly) training a set of pretext NN subsystems for performing S108-D pretext tasks using the generated S106 database of augmented training data sets. The set of pretext NN subsystems comprises at least two different pretext NN subsystems. The training S108 comprises a sub-step S108-A of selecting an augmented training data set from the generated S106 database. The training S108 further comprises a sub-step S108-B of cropping a patch from the selected S108-A augmented training data set. The cropping S108-B comprises cropping the medical imaging data set and the aggregated S106-B multi-mask of the augmented training data set at the same voxel location, and/or pixel location, for the multi-mask and the medical imaging data set. The training S108 further comprises a sub-step S108-C of generating a set of transformed patches. The generating S108-C of the set of transformed patches comprises performing at least one predetermined transformation operation on the cropped S108-B patch. The training S108 further comprises a sub-step S108-D of performing the pretext tasks using the set of pretext NN subsystems. One or more generated S108-C transformed patches are used as input for each pretext NN subsystem. Any one, or each, pretext task comprises classifying, and/or applying an inverse of, the at least one predetermined image-to-image transformation operation. The training further comprises determining a pretext NN subsystem-specific loss function. The pretext NN subsystem-specific loss function is indicative of a similarity of the output of the pretext NN subsystem and a mask within the aggregated S106-B multi-mask, and/or a similarity of the output of the pretext NN subsystem and medical imaging data comprised in the cropped patch. The at least two different pretext NN subsystems differ in the type of output. The type of output comprises a mask according to one of the masks within the aggregated S106-B multi-mask. Alternatively or in addition, the type of output comprises a classification of the predetermined image-to-image transformation operation. Further alternatively or in addition, the type of output comprises a reconstructed version of the (e.g., original, and/or cropped) medical imaging data (e.g., after applying the invers of the at least one predetermined image-to-image transformation operation).

The training S108 still further comprises a sub-step S108-E of modifying (and/or optimizing) each pretext NN subsystem within the set of pretext NN subsystems based on a predetermined combination (e.g., a weighted sum) of the task-specific loss functions of the at least two different pretext NN subsystems. The modifying (and/or optimizing) S108-E comprises modifying (and/or optimizing) one or more weights of the pretext NN subsystem.

The method 100 still further comprises a step S110 of pretraining the downstream NN for the novel image-to-image task to be performed on medical imaging data received from a medical scanner. The pretraining S110 of the downstream NN may be based on (e.g., at least) a subset of the modified S108-E weights of the pretext NN subsystems. Alternatively or in addition, the pretraining S110 of the downstream NN may be based on an output of a subset of layers (e.g., the output layer of an encoder, and/or an output layer of a decoder) of the set of pretext NN subsystems.

Optionally, the method 100 comprises a step S102 of selecting the set of existing trained image-to-image models for the step of generating S106 the database of augmented training data sets.

Alternatively or in addition, the method 100 may comprise a step S104 of receiving, from the at least one database, the pre-existing training data sets for the step of generating S106 the database of augmented training data sets.

Further alternatively or in addition, the method 100 may comprise a step S112, and/or a step S112', of training the downstream NN. The training S112 of the downstream NN may comprise initializing weights of the downstream NN based on the subset of the modified S108-E weights of the pretext NN subsystems. Alternatively or in addition, the training S112' may comprise a pretraining of the downstream NN for reproducing the output of the subset of the layers of the set of pretext NN subsystems.

The training S112; S112' may be further performed using a training database of medical imaging data in relation to the novel image-to-image task to be performed by the downstream NN.

Still further alternatively or in addition, the method 100 may comprise a step S114 of applying the trained S112; S112' downstream NN to an, in particular current (and/or newly acquired), medical imaging data set received from a medical scanner.

Figure 2:
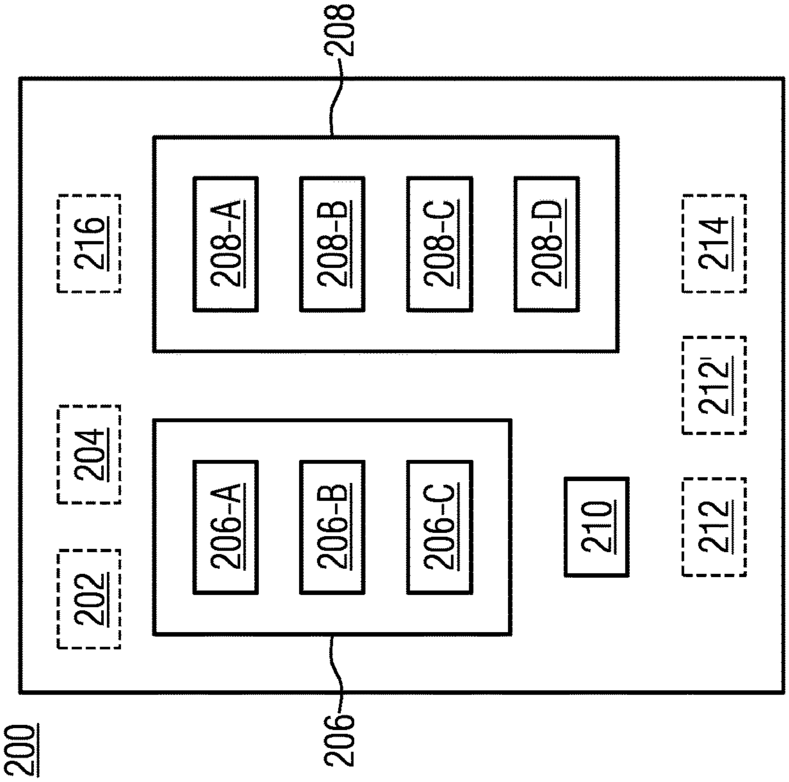
FIG. 2 is an overview of the structure and architecture of a computing device for a novel image-to-image task to be performed on medical imaging data received from a medical scanner according to a preferred embodiment of the present invention, which computing device may be configured to perform the method of FIG. 1.

FIG. 2 schematically illustrates an example of a computing device for pretraining a downstream NN for a novel image-to-image task to be performed on medical imaging data received from a medical scanner. The computing device is generally referred to by the reference sign 200.

The computing device 200 comprises a database generating module 206 configured for generating a database of augmented training data sets based on at least one database of pre-existing training data sets. The database generating module 206 comprises a mask creating sub-module 206-A configured for creating a mask in relation to each of a set of existing trained image-to-image models by applying each existing trained image-to-image model within the set to a pre-existing training data set within the at least one database of pre-existing training data sets. Each existing trained image-to-image model within the set of existing trained image-to-image models is trained for creating a mask in relation to a medical imaging data set comprised in at least one of the pre-existing training data sets. The database generating module 206 further comprises an aggregating sub-module 206-B configured for aggregating the created masks for the pre-existing training data set into a multi-mask. The database generating module 206 still further comprises an assembling sub-module 206-C configured for assembling the augmented training data set. The augmented training data set comprises the aggregated multi-mask and the medical imaging data set from the pre-existing training data set.

The computing device 200 further comprises a pretext task training module 208 configured for (in particular jointly) training a set of pretext NN subsystems for performing pretext tasks using the generated database of augmented training data sets. The set of pretext NN subsystems comprises at least two different pretext NN subsystems. The pretext task training module 208 comprises an augmented training data set selecting sub-module 208-A configured for selecting an augmented training data set from the generated database. The pretext task training module 208 further comprises a patch cropping sub-module 208-B configured for cropping a patch from the selected augmented training data set. The cropping comprises cropping the medical imaging data set and the aggregated multi-mask of the augmented training data set at the same voxel location, and/or pixel location, for the multi-mask and the medical imaging data set. The pretext task training module 208 further comprises a transformed patches generating module 208-C configured for generating a set of transformed patches. The generating of the set of transformed patches comprises performing at least one predetermined transformation operation on the cropped patch. The pretext task training module 208 further comprises a set of pretext NN subsystems 208-D configured for performing the pretext tasks. One or more generated transformed patches are used as input for each pretext NN subsystem 208-D. Any one, or each, pretext task comprises classifying, and/or applying an inverse of, the at least one predetermined image-to-image transformation operation. The training further comprises determining a pretext NN subsystem-specific loss function. The pretext NN subsystem-specific loss function is indicative of a similarity between the output of the pretext NN subsystem 208-D and a mask within the aggregated multi-mask, and/or a similarity between the output of the pretext NN subsystem 208-D and medical imaging data comprised in the cropped patch. The at least two different pretext NN subsystems 208-D differ in the type of output. The type of output comprises a mask according to one of the masks within the aggregated multi-mask. Alternatively or in addition, the type of output comprises a classification of the predetermined image-to-image transformation operation. Further alternatively or in addition, the type of output comprises a reconstructed version of the (e.g., original, and/or cropped) medical imaging data.

The pretext task training module 208 still further comprises a pretext NN subsystem modifying sub-module 208-E configured for modifying (and/or optimizing) each pretext NN subsystem 208-D within the set of pretext NN subsystems 208-D based on a predetermined combination of the task-specific loss functions of the at least two different pretext NN subsystems 208-D. The modifying (and/or optimizing) comprises modifying one or more weights of the pretext NN subsystem 208-D.

The computing device 200 still further comprises a downstream NN pretraining module 210 that is configured for pretraining the downstream NN for the novel image-to-image task to be performed on medical imaging data received from a medical scanner. The pretraining of the downstream NN may be based on (e.g., at least) a subset of the modified weights of the pretext NN subsystems 208-D. Alternatively or in addition, the pretraining of the downstream NN may be based on an output of a subset of layers (e.g., the output layer of an encoder, and/or an output layer of a decoder) of the set of pretext NN subsystems 208-D.

Optionally, the computing device 200 comprises an existing trained image-to-image model selecting module 202 configured for selecting the set of existing trained image-to-image models for the step of generating the database of augmented training data sets.

Alternatively or in addition, the computing device 200 may comprise a pre-existing training data set receiving module 204 that is configured for receiving, from the at least one database, the pre-existing training data sets for the step of generating the database of augmented training data sets.

Further alternatively or in addition, the computing device 200 may comprise a downstream NN training module 212 and/or 212' that is configured for training the downstream NN.

The training of the downstream NN, by the downstream NN training module 212, may comprise initializing weights of the downstream NN based on the subset of the modified weights of the pretext NN subsystems 208-D. Alternatively or in addition, the training of the downstream NN, by the downstream NN training module 212', may comprise a pretraining of the downstream NN for reproducing the output of the subset of the layers (e.g., the output layer of an encoder, and/or an output layer of a decoder) of the set of pretext NN subsystems 208-D.

Still further alternatively or in addition, the computing device 200 may comprise a downstream NN applying module 214 that is configured for applying the trained downstream NN to an, in particular current (and/or newly acquired), medical imaging data set received from a medical scanner.

The computing device 200 may still further comprise a memory, in particular for storing the database of augmented training data sets.

The computing device 200 may be configured for performing the method 100.

According to an embodiment, a system for pretraining a downstream NN for a novel image-to-image task to be performed on medical imaging data received from a medical scanner may comprise a computing device 200 and the downstream NN, which is configured for being pretrained by the downstream NN 210 pretraining module of the computing device.

According to another embodiment, a system for pretraining a downstream NN for a novel image-to-image task to be performed on medical imaging data received from a medical scanner may comprise any of the modules and sub-modules disclosed in the context of the computing device 200 in a distributed manner (e.g., distributed over multiple hardware components) and the downstream NN, which is configured for being pretrained by the downstream NN 210 pretraining module.

Any of the above systems may further comprise a memory for storing the database of augmented training data sets. Alternatively or in addition, any of the above systems may be configured for executing the method 100.

The inventive technique may also be denoted as large-scale image-to-image NN pretraining leveraging prior knowledge and self-supervised learning.

According to the inventive technique, a novel pretraining framework combines the power of self-supervised learning (SSL) with prior knowledge that may already be existing (e.g., in products, R&D projects, and/or open-source) in the form of trained artificial intelligence (AI) models, and/or full AI processing pipelines, for medical image-to-image model (and/or downstream NN) pretraining (e.g., encoder-decoder based architectures for segmentation, classification, and/or similar tasks). By successfully integrating prior knowledge, the models (and/or downstream NNs) can learn more efficiently while leveraging all available knowledge, leading to faster learning and better robustness.

Figure 3:
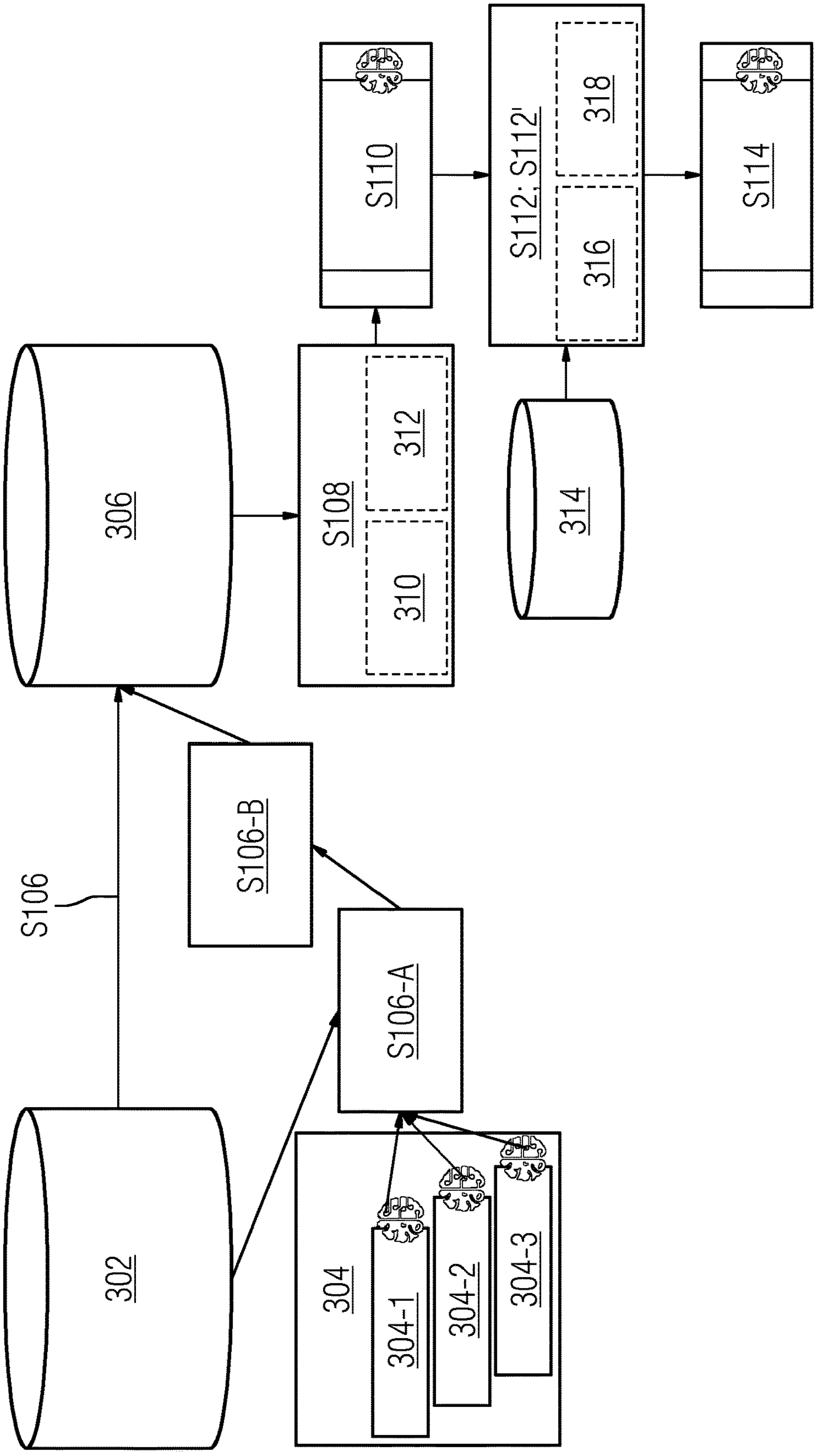
FIG. 3 shows a schematic illustrative embodiment of performing the method of FIG. 1.

As schematically illustrated in FIG. 3, the inventive technique is based on the three main steps S106, S108 and S110.

The inventive technique (e.g., comprising the method 100, the computing device 200, and/or a system), as illustrated at reference signs 302 and 304; 304-1; 304-2; 304-3 makes use of at least one database 302 of pre-existing training data sets (also denoted as large collection of images, e.g., from a massive medical image data lake). The inventive technique further makes use of a set of existing trained image-to-image models 304 (which may also be denoted as prior knowledge in the form of trained models) that can operate on medical image data sets (briefly also: images) comprised in the pre-existing training data sets. The trained image-to-image models 304 (collectively also denoted as existing pool of trained models, e.g., models for segmenting) may, e.g., be extracted from previous projects, products, shared by other institutions, and/or publicly available models.

A first class of trained image-to-image models 304-1 in FIG. 3 may comprise segmentation tasks for organs, e.g., the liver, and/or heart, of a patient (and/or, in particular human, body).

A second class of trained image-to-image models 304-2 in FIG. 3 may comprise segmentation tasks for structures, e.g., ribs, and/or knees, of a patient (and/or, in particular human, body).

A third class of trained image-to-image models 304-3 in FIG. 3 may comprise segmentation tasks for abnormalities, e.g., nodules, of a patient (and/or, in particular human, body).

The step S106-A in FIG. 3 may also be denoted as inference, and/or as predicting labels by applying each model to each available image.

The step S106-B in FIG. 3 may also be denoted as aggregation, and/or as combining all label results into multi-label masks.

The database 306 of augmented training data sets in FIG. 3 may also be denoted as large data lake with auto-generated labels (in particular available for each image).

The training S108 of the set of pretext NN subsystems may also be denoted as pretext, and/or as pretraining (e.g., for the downstream NN). At reference sign 310, an example of a pretext task may comprise a (e.g., multi-label, and/or multi-mask) segmentation task. At reference sign 312, as a further example of a pretext task, any SSL pretext task (e.g., comprising a classification, and/or application of an inverse of, a predetermined transformation operation) may be considered. In particular, the two pretext tasks 310; 312 in FIG. 3 may correspond to two different pretext NN subsystems, one with weakly supervised learning and the other one with SSL.

The step S110 in FIG. 3 may also be denoted as pretrained model. The step S112 or S112' in FIG. 3 may also be denoted as downstream training. At reference sign 316, the pretraining of the downstream NN may comprise an initialization of some weights based on some weights of the pretext NN subsystems, and/or the pretraining of the downstream NN may comprise reproducing outputs of some layers of the set of pretext NN subsystems (also denoted as knowledge distillation). At reference sign, 318, further training (e.g., after the pretraining) of the downstream NN may be performed. At reference sign 314 in FIG. 3, downstream task specific data and annotations may be used for the training of the downstream NN.

At reference sign S114 in FIG. 3, the downstream NN (also denoted as downstream model) may be applied.

If annotations for some (e.g., pretext, and/or downstream) tasks are available, the corresponding (e.g., downstream) NN and/or (e.g., pretext) NN subsystems (briefly also: models) may be further extended by generating, and/or training, new NNs and/or NN subsystems (also: models) based on those data and annotations, for instance by conventional supervised learning (e.g., as indicated at reference sign 314 in FIG. 3).

The training of the set of pretext NN subsystems according to the inventive technique provides rich features that can benefit the downstream NN in terms of better accuracy, faster training, and/or more stable training (e.g., compared to conventional NN training). According to the inventive technique, conventional SSL methods may be augmented by tasks designed to include prior knowledge (e.g., pseudo ground truths, and/or, in particular automatically, created masks), enabling a reuse of previously developed AI models in various applications. E.g., thereby the value of the previously developed AI models, and/or existing work, may be increased.

In the example of FIG. 3, the main steps of the inventive technique may be denoted as prerequisites comprising a large data lake of relevant data 302 (e.g., CT images), and a pre-existing pool 304 of trained (in particular segmentation) models trained to segment various organs 304-1, structures 304-2, and/or abnormalities 304-3.

In the example of FIG. 3, the steps at reference signs S106-A and S106-B may also be denoted as application of pre-existing models to large set of images to generate aggregated multi-label mask, combining results of many models.

In the example of FIG. 3, large-scale training S108 may be performed to generate a pretrained model S110 based on standard pretext tasks from self-supervised learning 312 in combination with a multi-label segmentation task 310 based on the automatically generated multi-label mask 306 from the previous step S106 (in particular available for each image).

In the example FIG. 3, at reference signs S112; S112' the pretrained model S110 may be utilized for one or more downstream tasks, e.g., by finetuning pretrained weights 316 on downstream task-specific data and annotations 314.

The main steps may alternatively be denoted as data generation S106, pretraining S108; S110 (and/or training of the pretext NN subsystems, e.g., for the downstream NN) and finetuning S112; S112'.

The data generation S106 may comprise running inferences of each existing trained image-to-image model on each medical imaging data set (briefly: image) in the database 302 (also denoted as data lake). Each existing trained image-to-image model is expected to produce S106-A an output result (such as a single- or multi-label segmentation mask) in case it detects a single or multiple organs, anatomies, and/or abnormalities). The masks are then aggregated S106-B into a multi-label mask, e.g., according to user-defined rules. The step S106-B may be be seen as transferring the knowledge preserved in existing trained image-to-image models onto an augmented training data set (also denoted as large data set).

In the pretraining S108; S110 (and/or training of the pretext NN subsystems, e.g., for the downstream NN), the images in the database 306 (also: data lake) in conjunction with the (in particular automatically) generated S106-A; S106-B multi-label masks are used to derive a loss function, which may also be denoted as loss signal, (e.g., according to the substep S108-D) to guide the training of a set of pretext NN subsystems 208-D (and/or a large model) based on the transferred knowledge of the existing trained image-to-image models (e.g., based on the previous step S106). At the same time, SSL pretext tasks may be employed to allow the (in particular weakly supervised learning) pretext NN subsystem (and/or model) to learn richer features, which may extract information different from, and/or orthogonal to, that from the multi-label masks. The output of the step S108 is the pretrained set of pretext NN subsystems (briefly: pre-trained model).

The finetuning S112; S112' may comprise that once the trained pretext NN subsystems (also denoted as pretrained model) is available, it can be utilized in the (e.g., supervised) learning process for downstream tasks, where one typically has a set of separate downstream task-specific training images and corresponding annotations available.

For example, some of the trained pretext NN subsystem (and/or pretrained model) weights may be used to initialize S110; S112 the downstream NN (also denoted as down-stream model), e.g., instead of random initialization. The full trained set of pretext NN subsystems (pretrained model) weights, or only parts of ist weights, may be used S112 (e.g., encoder only, and/or predetermined layers only).

Alternatively or in addition, model distillation (e.g., teacher-student approaches, and/or use of the output of a subset of layers of the pretext NN subsystem) techniques S112' may be employed. The model distillation may, e.g., be preferred in scenarios where the downstream NN (also: downstream model) is deployed on limited hardware resources, where running large NNS (also: large models) such as those used for training of the set of pretext NN subsystems (also denoted as pretraining) is not possible, and/or more generally, whenever compact models are preferred.

The step S108 of training the set of pretext NN subsystems may also be denoted as pretraining with joint multi-label weak supervision and SSL.

The step S108 may start with the data preprocessing steps S108-A; S108-B; S108-C (also denoted as data augmentation pipeline). One possible pipeline (and/or exemplary preprocessing) is schematically sketched in FIG. 4, in which at reference sign 402 an augmented training data set as input comprises a 2D image or a 3D image.

First, an image patch 404 is cropped S108-A from a random location in the image, and the contents of the image patch 404 are duplicated (e.g., as indicated by A" and B" at reference signs 404-A1 and 404-B1, respectively).

Second, a series of transformations is applied to the patches (in particular independently for the patches A" and B" at reference signs 404-A1 and 404-B1, respectively). E.g., the two patches may be randomly rotated (e.g., by discrete angles such as 90, 180 or 270 degrees along a randomly selected axis) yielding the patches A' and B' at reference signs 404-A2 and 404-B2, respectively, in FIG. 4. Alternatively or in addition, small regions, e.g., in the rotated patches, may be masked by replacing the voxels inside those regions with noise, yielding the patches A and B at reference signs 404-A3 and 404-B3, respectively, in FIG. 4.

The output of preprocessing steps S108-A; S108-B, S108-C may, e.g., comprise the patches A and B at reference signs 404-A3 and 404-B3, respectively, in FIG. 4. The output may be fed into the pretext NN subsystems.

It is noted that some of the transformation operations (also denoted as transformations, e.g., comprising the rotations and/or noise introduction) may be specifically designed to enable predetermined SSL pretext tasks. E.g., the applied random rotation operation may be stored and can serve as target for a "rotation recovery" pretext task, which attempts to recover the transformation operation from the rotated patch contents. Image perturbation (e.g., introducing noise) can be used to set up an image content reconstruction pretext task (such as: recover original voxel intensities of patch A' at reference sign 404-B2 from patch A at reference sign 404-B3). It is further noted that both pretext tasks may be set up without any manual annotations, and/or without any interactions (e.g., by an expert, in particular a medical practitioner) be required.

The substeps S108-B; S108-C (e.g., as described above) are applied to both the image (and/or volume in the case of 3D images) and the corresponding multi-mask (also denoted as multi-label mask), whereby the crop location for the image and the mask are identical and the same transformations are applied to the image patch A"_image and the mask patch A"_mask, as well as for image patch B"_image and mask patch B"_mask. Transformation operations at a pixel intensity level need only be applied to the image (e.g., the perturbation step is skipped for the mask, also denoted as label mask), e.g., due to an incompatibility between intensity and mask (and/or label) space.

In one embodiment of the inventive technique, one patch is cropped from each image and/or mask per training epoch. In another embodiment, two or more non-overlapping patches are cropped from each image and/or mask (which may, e.g., be relevant for a contrastive task as pretext task).

Figure 5A:
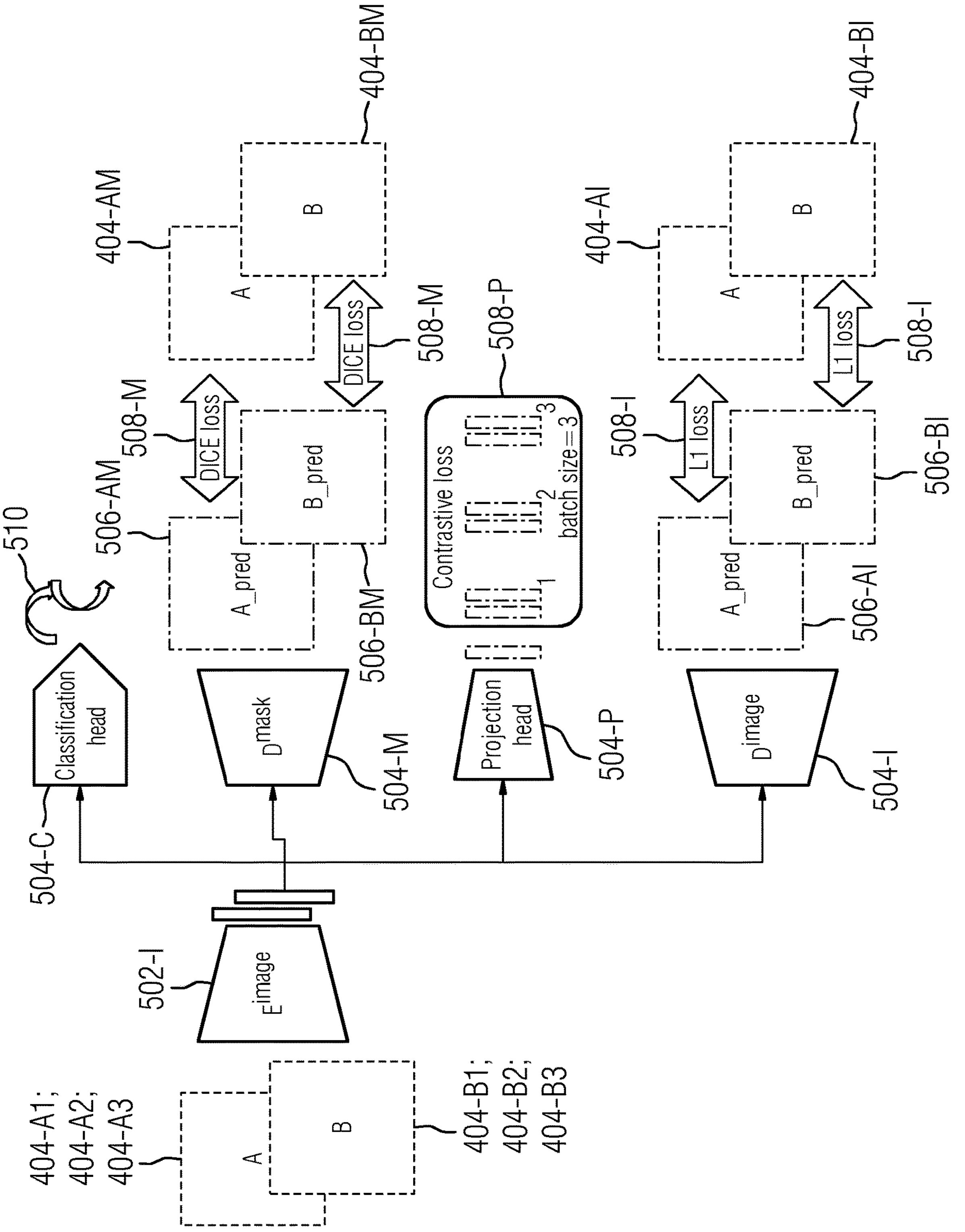
FIGS. 5A and 5B illustrate a first exemplary embodiment of combining a plurality of pretext training tasks, each performed by a pretext NN subsystem, for modifying each of the pretext NN subsystems according to the training of FIG. 1, wherein multiple pretext NN subsystems share an image encoder.
Figure 5B:
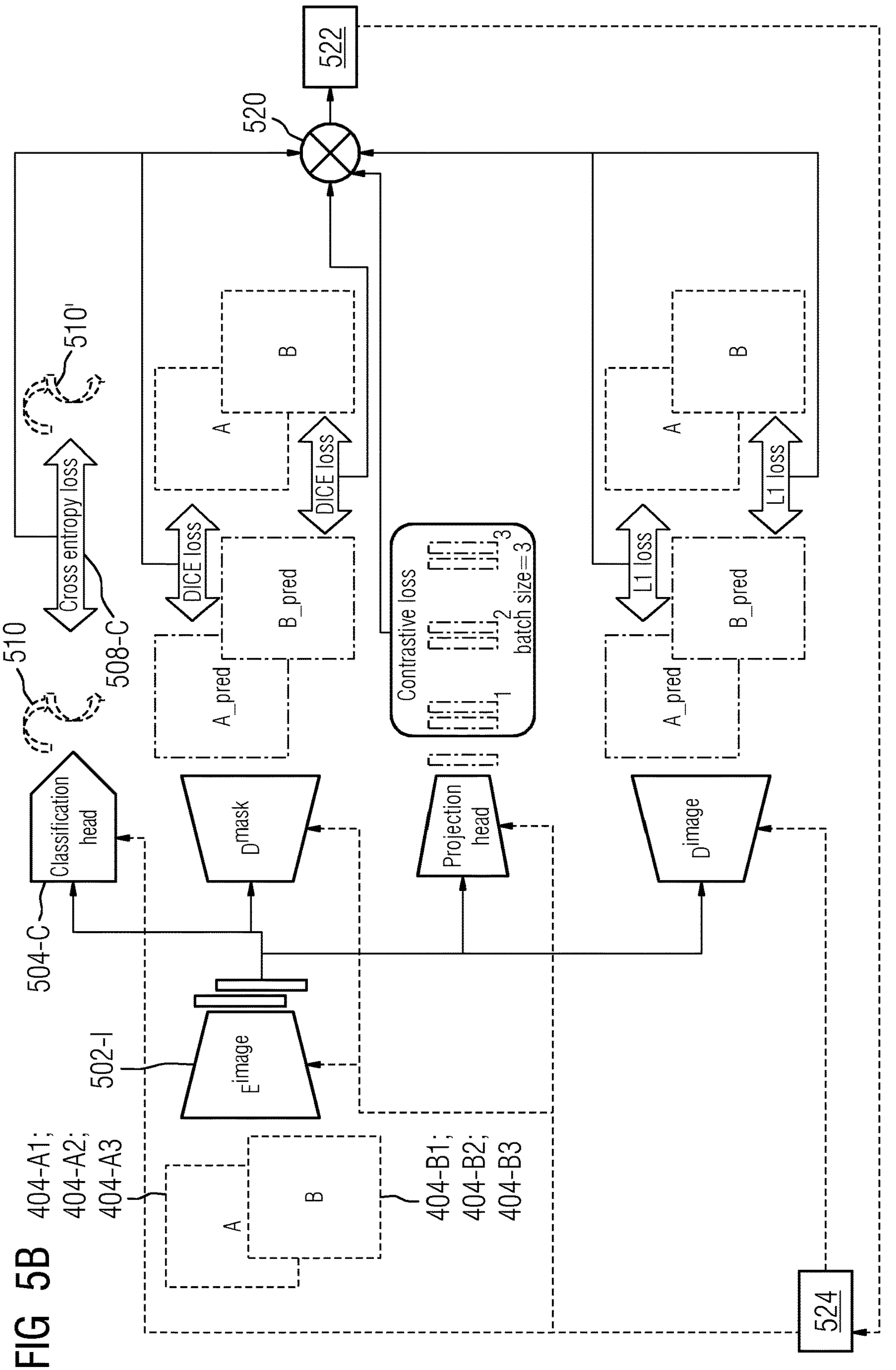

In FIGS. 5A and 5B, an illustrative example of a training setup for a set of pretext NN subsystems (also denoted as pretraining setup) is shown based on an encoder-decoder architecture, incorporating multiple SSL pretext tasks and a (e.g., multi-mask, and/or multi-label) weak supervision task.

It is noted that the inventive technique is agnostic to the type of pretext NN subsystems used for (e.g., image, and/or mask) encoder, and/or (e.g., image, and/or mask) decoder (e.g., each encoder, and/or decoder, may be of standard convolutional, or transformer-based, or mixed type).

The example illustrated in FIG. 5A shows a pretext NN subsystems training setup (also denoted as pretraining setup) involving three SSL pretext tasks and one weakly supervised segmentation task. Core network components include an encoder ($E^{image}$) at reference sign 502-I and two decoders ($D^{mask}$ and $D^{image}$) at reference signs 504-M and 504-I, respectively. Pretrained weights from $E^{image}$ at reference sign 502-I and $D^{image}$ at reference sign 504-M may be particularly useful in segmentation-like downstream tasks (e.g., performed by a trained downstream NN).

At reference signs 404-AI; 404-A2; 404-A3 and 404-Ba; 404-B2; 404-B3 the input to the image encoder ($E^{image}$) at reference sign 502-I is shown.

At reference sign 506-AI and 506-BI, the outputs of the image decoder ($D^{image}$) at reference sign 504-I is shown. By the combination of the image encoder ($E^{image}$) 502-I and the image decoder ($D^{image}$) 504-I, a reconstruction task as an example of a SSL pretext task is performed. The corresponding loss function of the reconstruction task in the example of FIG. 5A comprises an L1 loss, as indicated at reference sign 508-I. The combination of the image encoder ($E^{image}$) 502-I and the image decoder ($D^{image}$) 504-I, and/or the reconstruction task, may primarily operate on image intensities.

At reference sign 506-AM and 506-BM, the outputs of the mask decoder ($D^{mask}$) at reference sign 504-M is shown. By the combination of the image encoder ($E^{image}$) 502-I and the mask decoder ($D^{mask}$) 504-M, a weakly supervised segmentation task may be performed. The corresponding loss function may comprise a DICE loss as indicated at reference sign 508-M. At reference signs 404-AM; and 404-BM, the masks associated with the transformed image patches A and B (e.g., with reference signs 404-AI and 404-BI, respectively) are indicated, which are used for determining the DICE loss 508-M. The combination of the image encoder ($E^{image}$)

502-I and the mask decoder ($D^{mask}$) 504-M, and/or the weakly supervised segmentation task, may primarily operate on masks (and/or labels).

In the example illustrated in FIG. 5A, three SSL pretext tasks are employed besides the weakly supervised segmentation task. Besides the reconstruction task using the combination of the image encoder ($E^{image}$) 502-I and the image decoder ($D^{image}$) 504-I, a rotation task 510 uses the combination of the image encoder ($E^{image}$) 502-I and the classification head 504-C as SSL pretext task. The third SSL pretext task in FIG. 5A comprises a contrastive task, which uses the combination of the image encoder ($E^{image}$) 502-I and the projection head 504-P. The loss function of the contrastive task comprises a contrastive loss as indicated at reference sign 508-P.

The classification head 504-C and projection head 504-P may collectively be denoted as task-specific heads.

The goal of the weakly supervised segmentation task is to learn a mapping from a perturbed image patch to a (e.g., multi-) mask (and/or, in particular multi-, label), for which masks (and/or labels) were generated S106 using prior knowledge (and/or existing trained image-to-image models) and a database of pre-existing training data sets (also denoted as large set of images), but in particular without any additional manual annotation work.

In FIG. 5A, two SSL pretext tasks (namely, rotation and reconstruction) can operate on individual patches, while the third SSL pretext task (namely, contrastive) leverages the data augmentation pipeline producing two perturbed samples for each patch to define positive pairs for the contrastive loss 508-P. Negative pairs can be defined as embeddings from extracted patches of other images in the same mini batch, or can be based on non-overlapping patches extracted from the same image.

FIG. 5B provides additional details for training of the pretext NN subsystems (also denoted as pretraining setup) of FIG. 5A by illustrating both the forward propagation (and/or computing predictions based on current state and/or weights of pretext NN systems) and the backward propagation (and/or, based on loss, computing weight updates).

In FIG. 5B, the column of classification head 504-C, mask decoder ($D^{mask}$) 504-M, projection head 504-P and image decoder ($D^{image}$) 504-I can be viewed as the forward computation, which takes the current pretext NN subsystem weights (e.g., for each encoder 502-I, pretraining-task specific decoders 504-M; 504-I, and/or other heads 504-C; 504-P) to compute a pretext task (also denoted as pretraining-task) specific prediction from the input data 404-Ai; 404-Bi (with i=1,2,3).

The column in FIG. 5B comprising the rotation task 510, outputs 506-AM; 506-BM of the mask decoder ($D^{mask}$) 504-M, the outputs of the projection head 504-P, the outputs 506-AI; 506-BI of the image decoder ($D^{image}$) 504-I as well as the pretext task (also denoted as pretraining-task) comprises the specific loss computations as indicated at reference signs 508-C; 508-M; 508-P; 508-I by taking into account both the predictions (and/or the output 510 of the classification head 504-C, the outputs 506-AM; 506-BM of the mask decoder ($D^{mask}$) 504-M, the outputs of the projection head 504-P, and the outputs 506-AI; 506-BI of the image decoder ($D^{image}$) 504-I) and targets (corresponding to the rotation at reference sign 510', masks 404-AM; 404-BM and images 404-AI; 404-BI).

At reference sign 520 in FIG. 5B, a loss aggregation (e.g., via a weighted sum of multiple individual losses 508-C; 508-M; 508-P; 508-I) is schematically illustrated at reference sign 520, based on which at reference sign 522 an optimization is performed (e.g., based on ADAM, and/or another stochastic gradient descent optimization algorithm, SGD).

At reference sign 524 in FIG. 5B, the weights of the pretext NN subsystems (e.g., comprising image encoder ($E^{image}$) 502-I, image decoder ($D^{image}$) 504-I, mask decoder ($D^{mask}$) 504-M, classification head 504-C and projection head 504-P) are updated based on the aggregated loss (and/or loss aggregation 520).

The updating of the weights (and/or the training of the pretext NN subsystems) may be iterative.

In the example of FIGS. 5A and 5B, the contrastive task (e.g., comprising the pretext NN subsystem of image encoder ($E^{image}$) 502-I and projection head 504-P) is purely self-supervised, as it is based on images only and does not require any additional information, and/or user input. E.g., cropped and transformed image patches 404-Ai; 404-Bi (with i=1,2,3) are run through image encoder ($E^{image}$) 502-I, and the contrastive projection head 504-P to compute a contrastive loss function (briefly also: contrastive loss) 508-P based on positive and negative pairs. Positive pairs may correspond to embeddings from the same image, and/or the same patch (e.g., the same value i=1,2,3 for both members of a pair). Negative pairs may correspond to embeddings from different images, and/or different patches (e.g., different values i and j for the two members of a pair).

Figure 6:
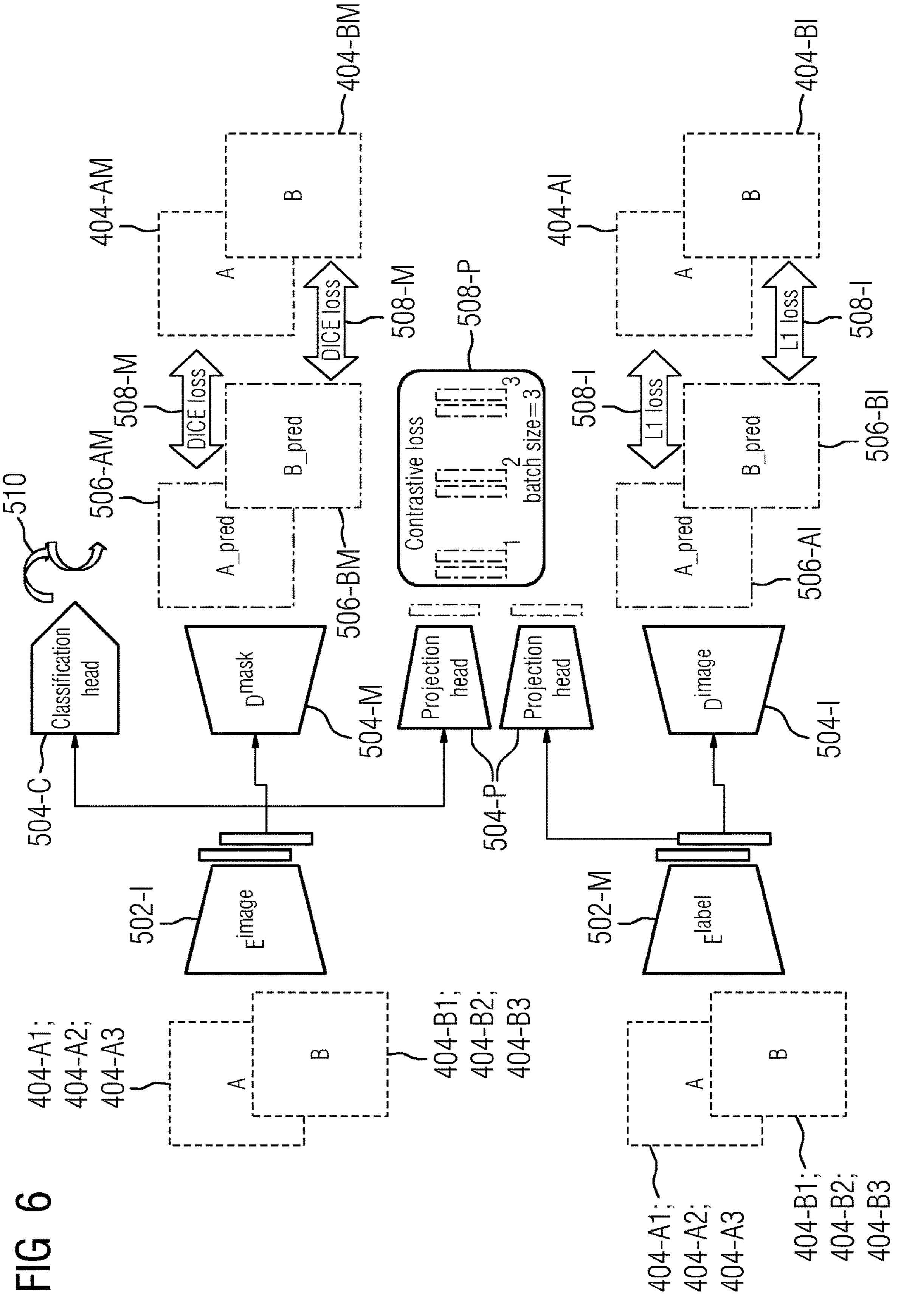
FIG. 6 illustrates a second exemplary embodiment of combining a plurality of pretext training tasks, each performed by a pretext NN subsystem, for modifying each of the pretext NN subsystems according to the training of FIG. 1, wherein multiple pretext NN subsystems share an image encoder, and/or a projection head.

In another example of the training setup for the pretext NN subsystems (also denoted as pretraining setup), as indicated in FIG. 6, an additional mask encoder ($E^{label}$) 502-M is employed, whose goal is to learn a meaningful mask (and/or) embedding, similarly to the image encoder ($E^{image}$) 502-I for image embeddings. Embeddings of corresponding mask patches and image patches (e.g., collectively denoted by the reference signs 404-Ai and 404-Bi with i=1,2,3 as the inputs of the encoders 502-I; 502-M in FIG. 6) may then define the positive pairs (e.g., instead of corresponding image patches only) in a modified version of the contrastive task to encourage similar embedding space for image- and mask (and/or label)-derived representations. E.g., the contrastive task in FIG. 6 may make use of two projection heads 504-P, one based input image patches, and the other one based on input mask patches.

In FIG. 6, the masks generated previously in the step S106 (e.g., as not pure imaging information, but instead additional source of information from the database of augmented training data sets, which may also be denoted as pre-existing pool of existing trained image-to-image models, e.g., whose existing trained image-to-image models may have generated via supervised learning, and/or based on user input, and/, in particular manual, annotations) may be taken into account in the contrastive loss function (briefly: contrastive loss) 508-P. Hence, the contrastive task in the example of FIG. 6 may be denoted as SSL with weak supervision.

As a variation of the example in FIG. 6, the reconstruction task (e.g., using the combination of the image encoder ($E^{image}$) 502-I and the image decoder ($D^{image}$) 504-I) may be modified to learn a mapping from a mask (and/or label) embedding to image intensities. E.g., the reconstruction task in FIG. 6 may be denoted as SSL with weak supervision.

In FIG. 6, the (in particular SSL) rotation task and (in particular weakly supervised) segmentation task remain unchanged as compared to the example of FIGS. 5A and 5B, while an additional mask encoder ($E^{label}$) 502-M is introduced, which maps mask (and/or label) patches to embeddings. Those embeddings can then be fed into the contrastive task and/or can used in the image reconstruction task, whereby any one of the contrastive task, and/or the reconstruction task, may change from SSL to SSL with weak supervision.

The example of FIG. 6 may be extended analogously to FIG. 5B in terms of the loss aggregation, optimization and update of weights of the pretext NN subsystems.

The scope of the inventive is not limited to the exact setups illustrated in FIGS. 5A, 5B and 6. Other variations, combinations, and/or extensions are possible. For example, additional SSL pretext tasks can be included, the different pretext and weak supervision tasks can be learned, e.g., in a multi-task setup.

Crawshaw [5] provides a survey of existing techniques for multi-task learning using NNs, where one or more of the tasks are the target tasks and/or applications (corresponding to the "downstream" tasks of the present invention). However, Crawshaw in [5] does not illustrate or provide details regarding the combination of weak supervision and self-supervision in an attempt to generate a (e.g., at least to a certain degree) downstream-task-agnostic pretrained NN. By contrast, according to the inventive technique, the pretraining and application to downstream tasks are (e.g., clearly) separated, and the focus is on the novel way of pretraining, where weak- and self-supervision are combined for image-to-image NNs (and/or pretext NN subsystems).

Alternatively or in addition, the inventive technique focuses on medical imaging data, comprising, e.g., 2D and/or 3D patient or organ scans, and/or static and/or temporally-resolved images. On the other hand, [5] is coming from a "natural images" (photos, . . . ) perspective, which brings its own and sometimes very different challenges as compared to medical imaging data.

One reason for the very different challenges comprises the difference in domain. Natural images capture an extensive diversity of objects (and/or subjects), while in medical imaging, the acquired data is (e.g., relatively) constrained to medically-relevant data, objects, and/or structures, such as organs, vessels, and/or bones. Alternatively or in addition, functional data (e.g., for scans using SPECT, and/or PET) of medical imaging may significantly differ from those of natural images.

Another reason for the very different challenges of "natural images" versus medical imaging comprises the nature of image acquisition. A pinhole camera (or similar) is conventionally used for natural images, with specific projection geometry and properties, whereas (e.g., a lot more) diverse acquisition protocols, diverse properties, and/or divers geometries are used in medical imaging. For example, X-ray images are typically acquired with parallel projection geometry, and the X-rays penetrate (and/or pass through) the body, while natural photography is done via a pinhole-like camera, by which in particular non-parallel rays are captured, and the rays captured do not pass through the body, but reflect from the surface.

The training of the pretext NN subsystems (also denoted as pretraining) may be based on the inventive technique, e.g., as described. The resulting rich features can benefit one or more downstream NNs (and/or downstream tasks) in multiple ways, in particular in terms of better accuracy, faster convergence, and/or more stable training.

Alternatively or in addition, the conventional SSL pretext tasks (also denoted as SSL methods) may be augmented by pretext tasks designed to include prior knowledge, enabling the reuse of existing trained image-to-image models (also denoted as previously developed AI models) in various applications, and thus increasing the value of existing work (e.g., comprising the existing trained image-to-image models).

Figure 7:
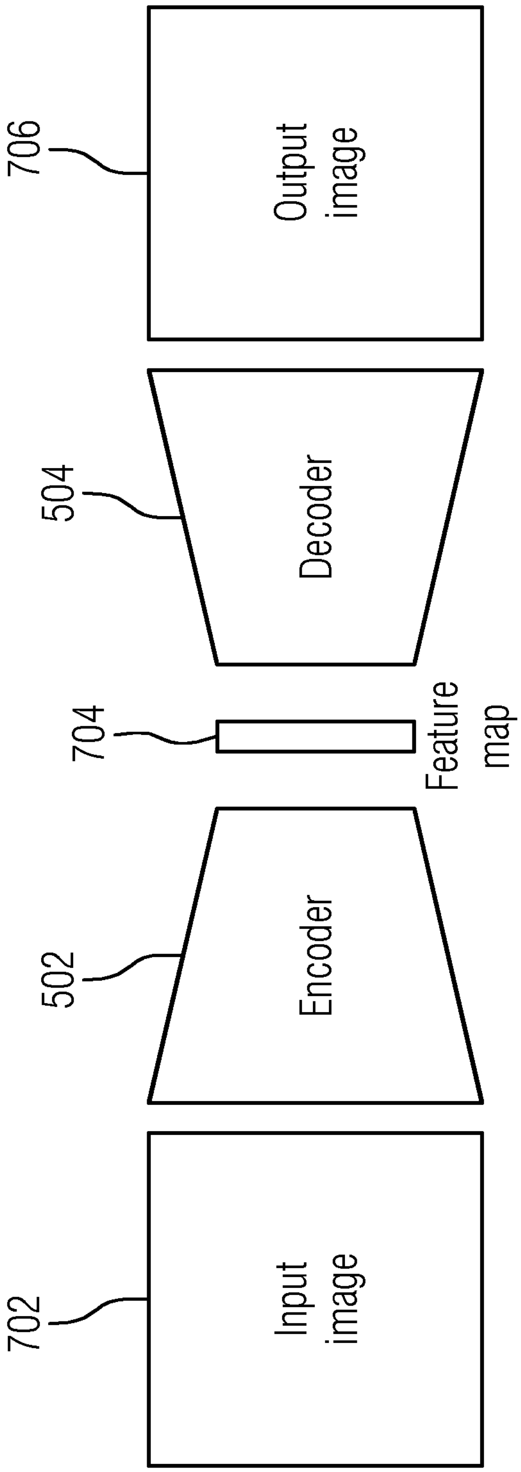
FIG. 7 shows an exemplary embodiment of a downstream NN.

A core artificial NN architecture used for the inventive technique may comprise a class of image-to-image encoder-decoders, as indicated in FIG. 7.

FIG. 7 shows an example of a generic image-to-image encoder-decoder architecture as an example of a NN architecture.

The encoder 502 in the example of FIG. 7 comprises a NN (e.g., a convolutional neural network, CNN, and/or a transformer) that takes an input image 702 (e.g., represented by a 2D or 3D pixel matrix) and converts it into a feature map 704, which can be seen as a different representation of the input image 702. The decoder 504 in the example of FIG. 7 comprises another NN (e.g., another CNN), that takes that feature map 704 as input and converts it back into an output image 706, which is as close as possible to the intended output (e.g., the output may be same as encoder input, as tested, and/or performed, by a reconstruction task; and/or the output may be a segmentation mask, as obtained by a segmentation task).

Typical architectures (e.g., for the downstream NN, and/or the pretext NN subsystems) used in medical imaging comprise, e.g., a CNN-based U-Net [6], or recently also transformer-based architectures (e.g., see reference [1], where the overall structure of the network can be like a U-Net, but the encoder consists of a transformer instead of a CNN). Other variations of the NN (e.g., the downstream NN, and/or the pretext NN subsystems) are possible.

Image-to-image models (also denoted as image-to-image NNs or image-to-image transformations) may be used for various applications such as image segmentation, image denoising, image reconstruction, and/or image style transfer (e.g., to convert CT-like image to MR-like images).

Image segmentation and image reconstruction are used in various embodiments of the inventive technique, e.g., in FIGS. 5A, 5B and 6, as pretext tasks. More precisely, in the inventive pretext NN subsystem (also denoted as pretraining) architecture of FIGS. 5A and 5B, one encoder is used to convert the image into a feature map, and two different decoders are used as "heads" for two different tasks, namely segmentation and reconstruction.

In further embodiments, (e.g., useful) pretext tasks may extend beyond pure encoder-decoder type networks. E.g., the rotation pretext task in FIGS. 5A and 5B uses the encoder, but instead of a decoder as the head, it may use a different type of architecture, such as a multi-layer perceptron, which takes the feature map and converts it into a multi-class prediction. For example, the pretext NN subsystem output may be a probability value for each defined class. E.g., classes may be set up to represent rotations by 90 degrees around each image axis, which corresponds to four classes for 3D images, namely {no rotation, 90° around x-axis, 90° around y-axis, 90° around z-axis}. Other options of defining (e.g., discrete) classes (e.g., comprising other values of angular rotations, and/or flips across some image plane) and/or probability values are possible.

Figure 4:
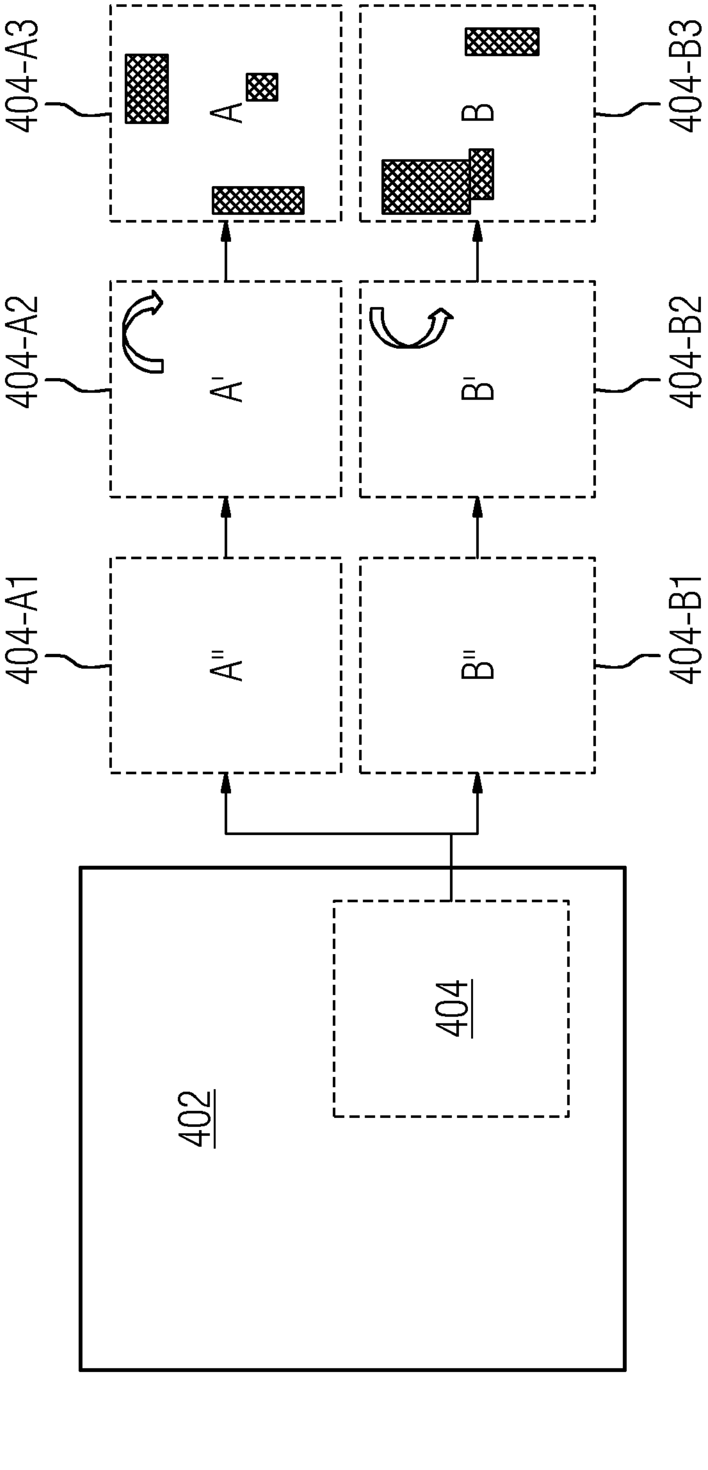
FIG. 4 schematically illustrates examples of cropping a patch and performing multiple transformation operations for generating a set of transformed patches for training a set of pretext NN subsystems according to the method of FIG. 1.

Other potentially useful pretext tasks in the context of 3D medical imaging, in particular when the type of intended downstream NN (and/or downstream task) comprises an image segmentation (and/or a similar task), beyond what was already been disclosed above in the context of FIGS. 4, 5A and 5B as well as 6, 7 may comprise shuffling of image slices and having the associated pretext NN subsystem reconstruct the original order (and/or, e.g., identify if shuffling happened or not); performing a "Jigsaw puzzle", which may be similar to slice shuffling, but instead of taking slices, takes image patches and shuffles them in the image; inpainting (e.g., removing, and/or obfuscating predetermined regions in the image and having the associated pretext NN subsystem identify that obfuscation happened, and/or reconstruct the original pixel, and/or voxel, intensities); and/or relative position prediction.

Additional details and examples (e.g., of transformation operations according to the substeps S108-B; S108-C) may be found in the chapter "Self-supervised learning approaches" in [7], which is incorporated herein by reference.

Several variations of the proposed pretraining framework have already been implemented, and successful experiments were conducted utilizing an existing model pool of over 30 different existing trained image-to-image models (as prior knowledge) and a large CT image database consisting of almost 25 million digital imaging and communications in medicine, briefly: DICOMS (correspond to ca. 85.000 CT volumes). The trained S108 set of pretext NN subsystems (and/or the pretrained model) (in particular comprising an, e.g., image, encoder and, e.g., mask, decoder) was then finetuned to various downstream tasks (and/used for pretraining various downstream NNs according to the step S110), where a significant boost in test performance could be observed in many instances, as well as more stable training and faster convergence.

In each of the FIGS. 8A, 8B, 8C, 9A, 9B, 9C, 10A, 10B and 10C, at reference sign 806 conventional training (e.g., using random initial weights) of a downstream NN is used, and at reference sign 808, pretraining of the downstream NN using the inventive technique is used.

Figure 8C:
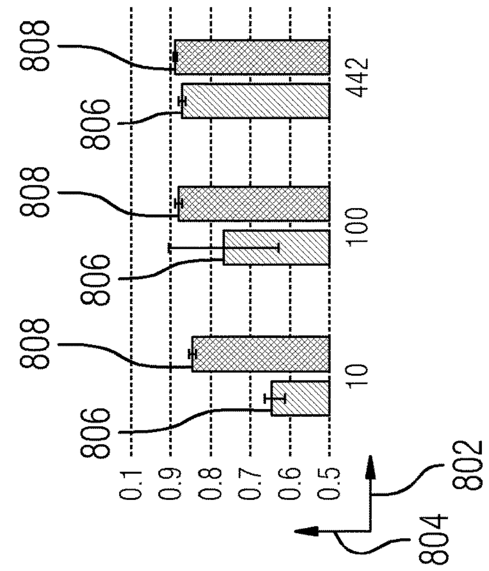
FIGS. 8A, 8B, and 8C show exemplary performance comparisons between a conventional training of a downstream NN and using the inventive pretraining of the downstream NN for segmentations of the esophagus, liver and multi rips, respectively, wherein the quality of the training is represented by a DICE score.
Figure 8B:
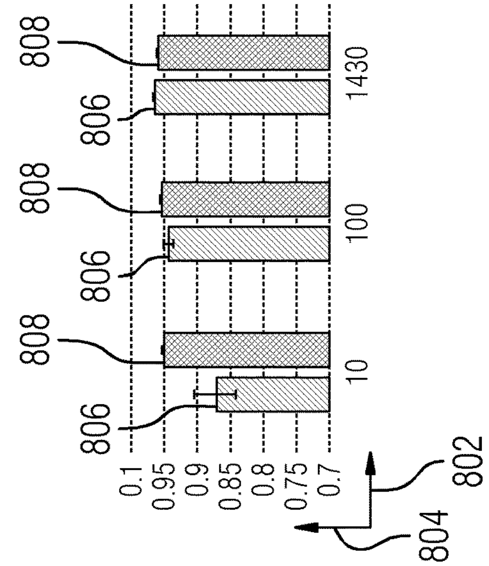
Figure 8A:
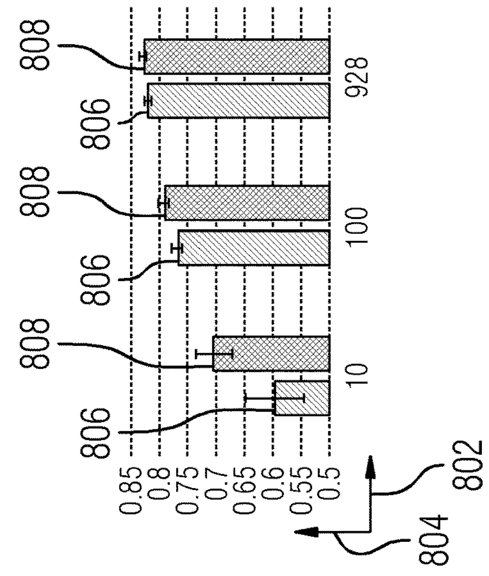

FIGS. 8A, 8B and 8C show examples of better (e.g., test) performance of downstream NNs for segmentations of the esophagus, liver, and multi-rips, respectively, when pretrained according to the inventive technique.

In FIGS. 8A, 8B and 8C, downstream training starting from randomized network weights ("from scratch") at reference sign 806 is compared to downstream training starting from the pretrained weights according to the inventive technique at reference sign 808. All training parameters were kept identical to enable fair comparison. As one can see, the DICE score at reference sign 804 on the test data set (e.g., which was not seen during training) can be significantly improved (in particular larger) when pretraining according to the inventive technique is leveraged. The benefits are more pronounced when less training data is available. The x-axis, as indicated at reference sign 802, on each plot shows the number of training samples used for training the corresponding downstream NN.

Figure 9C:
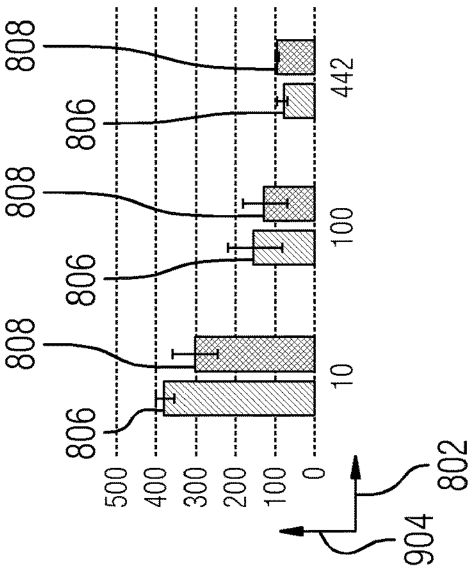
FIGS. 9A, 9B, and 9C show exemplary convergence comparisons between a conventional training of a downstream NN and using the inventive pretraining of the downstream NN for segmentations of the esophagus, liver, and multi rips, respectively, wherein the quality of the training is represented by the number of epochs required until the downstream NN converges.
Figure 9B:
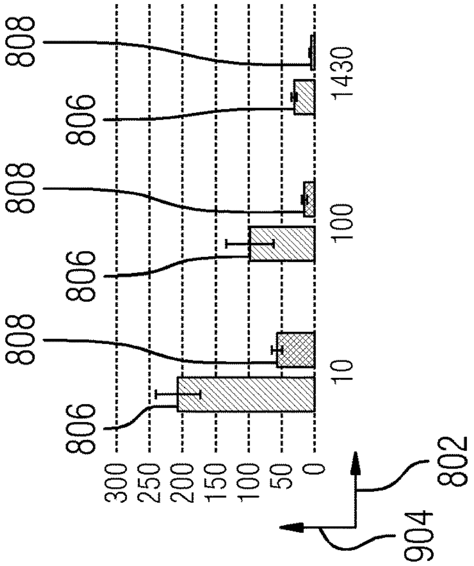
Figure 9A:
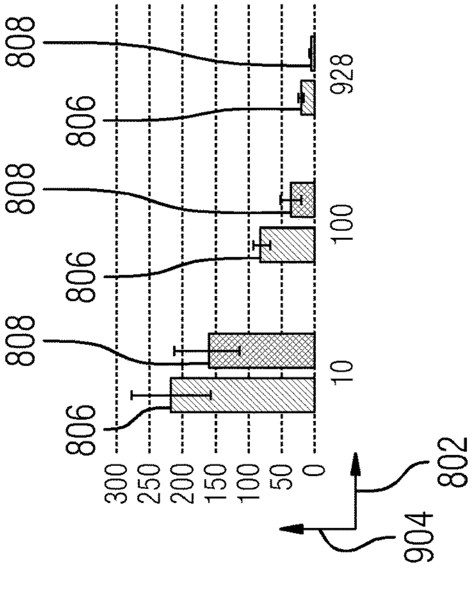

FIGS. 9A, 9B and 9C show examples of faster convergence in terms of the number of epochs until the downstream NN (and/or the downstream model) converged (e.g., a lower number of epochs at reference sign 904 corresponds to better convergence) when training from scratch, as indicated at reference sign 806, versus, as training from the inventive pretrained, as indicated at reference sign 808. FIGS. 9A, 9B and 9C show segmentations of the esophagus, liver, and multi-rips, respectively.

The pretrained version at reference sign 808 significantly outperforms training from scratch at reference sign 806 in eight of the nine experiments performed. Faster training means reduced resources use. Alternatively or in addition, faster training can enable faster (e.g., downstream) NN (and/or AI) product development cycles.

Figure 10A:
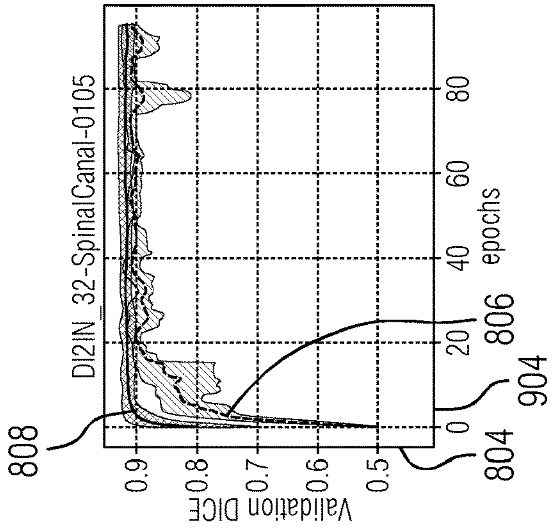
FIGS. 10A, 10B, and 10C show exemplary training stability comparisons between a conventional training of a downstream NN and using the inventive pretraining of the downstream NN for segmentations of the spinal canal, a bronchus, and a femoral head, respectively, wherein the stability of the training is represented in terms of the DICE score plotted against the number of epochs used for the training.
Figure 10B:
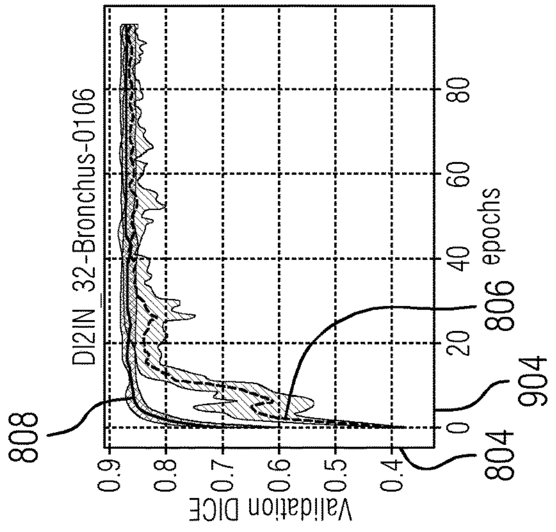
Figure 10C:
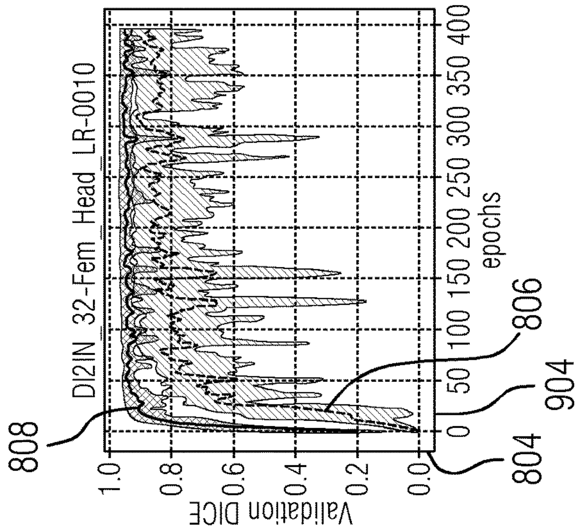

FIGS. 10A, 10B and 10C show examples of better training stability for spinal canal, bronchus, and femoral head segmentations, respectively. The plots in FIGS. 10A, 10B and 10C show at reference sign 804 the DICE score (where higher is better, e.g., in terms of training performance) on validation at each epoch, as indicated at reference sign 904, during training for the corresponding segmentation downstream tasks.

In FIGS. 10A, 10B and 10C, the solid line (at reference signs 808 and 806 for making use of the inventive pretraining and conventional training, respectively) denotes the mean, and the shaded areas show the minimum and/or maximum across multiple (typically n=5) runs of the same experiment (e.g., wherein the only variation is a different seed to initialize the RNG used for train/validation split, and/or standard data augmentations, e.g., noise). In each example of FIGS. 10A, 10B and 10C, only 10 training images may be used. As one can see, not only do the pretrained downstream NNs 808 outperform the training from scratch 806 throughout the entire training process according to the validation DICE metric 804, but the pretrained downstream NNs 808 also reach a plateau much faster and show significantly less variations and/or less fluctuations (i.e., a better training stability and/or robustness) than the conventionally trained downstream NNs 806. Similar observations were made for various other segmentation downstream tasks (and/or corresponding downstream NNs).

The inventive technique comprises a computer-implemented method for pretraining a downstream NN for a novel image-to-image task to be performed on medical imaging data received from a medical scanner. A database of augmented training data sets is generated based on at least one database of pre-existing training data sets. A set of at least two pretext NN subsystems are (in particular jointly) trained for performing (in particular partly self-supervised and partly weakly supervised) pretext tasks using the generated database of augmented training data sets. The downstream NN is pretrained for the novel image-to-image task to be performed on medical imaging data received from a medical scanner. The pretraining is based on a subset of the modified weights of the pretext NN subsystems, and/or on an output of a subset of layers of the set of pretext NN subsystems.

Wherever not already described explicitly, individual embodiments, or their individual aspects and features, described in relation to the drawings can be combined or exchanged with one another without limiting or widening the scope of the described invention, whenever such a combination or exchange is meaningful and in the sense of this invention. Advantages which are described with respect to a particular embodiment of present invention or with respect to a particular figure are, wherever applicable, also advantages of other embodiments of the present invention.

LIST OF CITED DOCUMENTS

[1] Tang et al.: "Self-Supervised Pre-Training of Swin Transformers for 3D Medical Image Analysis", https://doi.org/10.48550/arXiv.2111.14791

[2] Taleb et al.: "3D Self-Supervised Methods for Medical Imaging", NeurIPS 2020

[3] Ghesu et al.: "Self-supervised Learning from 100 Million Medical Images", https://doi.org/10.48550/arXiv.2201.01283

[4] Haghighi et al.: "DiRA: Discriminative, Restorative, and Adversarial Learning for Self-supervised Medical Analysis", Image https://doi.org/10.48550/arXiv.2204.10437

[5] Crawshaw: “Multi-Task Learning with Deep Neural Networks: A Survey”, https://doi.org/10.48550/arXiv.2009.09796
[6] Ronneberger et al.: “U-Net: Convolutional Networks for Biomedical Image Segmentation” MICCAI, 2015, https://link.springer.com/chapter/10.1007/978-3-319-24574-4_28
[7] Shurrab et al.: “Self-Supervised Learning Methods and Applications in Medical Imaging Analysis: A Survey”, https://arxiv.org/pdf/2109.08685.pdf
[8] Dian Qin et al.: “Efficient Medical Image Segmentation Based on Knowledge Distillation”, https://arxiv.org/abs/2108.09987v1
[9] Hatamizadeh et al. “UNETR: Transformers for 3D Medical Image Segmentation”, https://arxiv.org/abs/2103.10504

LIST OF REFERENCE SIGNS

100 Method for pretraining a downstream NN
S102 Step of selecting existing trained image-to-image models
S104 Step of receiving pre-existing training data sets
S106 Step of generating a database of augmented training data sets
S106-A Sub-step of creating a mask in relation to each existing trained image-to-image model
S106-B Sub-step of aggregating the created masks
S106-C Sub-step of assembling the augmented training data set
S108 Step of training a set of pretext NN subsystems
S108-A Sub-step of selecting an augmented training data set
S108-B Sub-step of cropping a patch
S108-C Sub-step of generating a set of transformed patches
S108-D Sub-step of performing the pretext tasks
S108-E Sub-step of modifying each pretext NN subsystem
S110 Step of pretraining the downstream NN
S112; S112' Step of training the downstream NN
S114 Step of applying the trained downstream NN
200 Computing device
202 Existing trained image-to-image model selecting module
204 Pre-existing training data set receiving module
206 Database generating module
206-A Mask creating sub-module
206-B Aggregating sub-module
206-C Assembling sub-module
208 Pretext task training module
208-A Augmented training data set selecting sub-module
208-B Patch cropping sub-module
208-C Transformed patches generating module
208-D Pretext NN subsystem
208-E Pretext NN subsystem modifying sub-module
210 Downstream NN pretraining module
212 Downstream NN training module
214 Downstream NN applying module
302 Database of pre-existing training data sets
304; 304-X Existing trained image-to-image model
306 Database of augmented training data sets
310 Pretext NN for performing a pretext task outputting a mask
312 Pretext NN for performing a pretext task comprising a (e.g., inverse) transformation operation
314 Training database for the downstream NN
316 Downstream NN initialization by some weights of the pretext NN subsystem, and/or pretraining by an output of a layer of a pretext NN subsystem
316 Downstream NN training
402 Medical imaging data set with multi-mask mask
404 Patch
404-AX Transformed patch (X=1,2,3)
404-BX Transformed patch (X=1,2,3)
502 Encoder
502-I Image encoder
502-M Mask encoder
504 Decoder
504-I Image decoder
504-M Mask decoder
504-C Classifier head
504-P Projection head
506-AM; Output of mask decoder
506-BM
506-AI; Output of image decoder
506-BI
508-I Image loss function
508-M Mask loss function
508-C Cross-entropy loss
508-P Contrastive loss
510; 510' Rotation recovery
520 Loss aggregation
522 Optimization of encoder, decoder & head weights
524 Update of encoder, decoder & head weights
702 Encoder
704 Medical imaging data set as input for pretrained NN
706 Output, in particular mask, of pretrained NN
802 Number of training data sets
804 DICE score
806 Training of the downstream NN without pretraining
808 Training of the downstream NN with pretraining
904 Number of training epochs

The invention claimed is:

1. A computer implemented method for pretraining a downstream neural network (NN) for a novel image-to-image task to be performed on medical imaging data received from a medical scanner, comprising the method steps of:
- generating a database of augmented training data sets based on at least one database of pre-existing training data sets, wherein generating an augmented training data set for the database of augmented training data sets from an existing training data set comprises:
  - creating a mask in relation to each of a set of existing trained image-to-image models by applying each existing trained image-to-image model within the set to a pre-existing training data set within the at least one database of pre-existing training data sets, wherein each existing trained image-to-image model within the set of existing trained image-to-image models is trained for creating a mask in relation to a medical imaging data set comprised in at least one of the pre-existing training data sets;
  - aggregating the created masks for the pre-existing training data set into a multi-mask; and
  - assembling the augmented training data set, wherein the augmented training data set comprises the aggregated multi-mask and the medical imaging data set from the pre-existing training data set;
- training a set of pretext NN subsystems for performing pretext tasks using the generated database of augmented training data sets, wherein the set of pretext NN subsystems comprises at least two different pretext NN subsystems, wherein the training comprises:

selecting an augmented training data set from the generated database;

cropping a patch from the selected augmented training data set, wherein the cropping comprises cropping the medical imaging data set and the aggregated multi-mask of the augmented training data set at the same voxel location and/or pixel location for the multi-mask and the medical imaging data set;

generating a set of transformed patches, wherein the generating of the set of transformed patches comprises performing at least one predetermined transformation operation on the cropped patch;

performing the pretext tasks using the set of pretext NN subsystems, wherein one or more generated transformed patches are used as input for each pretext NN subsystem, wherein any one, or each, pretext task comprises classifying, and/or applying an inverse of, the at least one predetermined transformation operation, wherein the training further comprises determining a pretext NN subsystem-specific loss function, wherein the pretext NN subsystem-specific loss function is indicative of a similarity of an output of the pretext NN subsystem and a mask within the aggregated multi-mask, and/or a similarity of the output of the pretext NN subsystem and medical imaging data, comprised in the cropped patch, wherein the at least two different pretext NN subsystems differ in a type of output, wherein the type of output comprises a mask according to one of the masks within the aggregated multi-mask, a classification of the at least one predetermined transformation operation, and/or a reconstructed version of the medical imaging data; and modifying each pretext NN subsystem within the set of pretext NN subsystems based on a predetermined combination of task-specific loss functions of the at least two different pretext NN subsystems, wherein the modifying comprises modifying one or more weights of the pretext NN subsystem; and pretraining the downstream NN for the novel image-to-image task to be performed on medical imaging data received from a medical scanner, wherein the pretraining is based on a subset of the one or more modified weights of the pretext NN subsystems, and/or based on an output of a subset of layers of the set of pretext NN subsystems.

2. The method according to claim 1, wherein the method further comprises at least one of the steps of:

selecting the set of existing trained image-to-image models for the step of generating the database of augmented training data sets; and receiving, from the at least one database, the pre-existing training data sets for the step of generating the database of augmented training data sets.

3. The method according to claim 1, wherein the method further comprises at least one of the steps of:

training the downstream NN by initializing weights of the downstream NN based on the subset of the modified weights of the pretext NN subsystems, wherein the training is performed using a training database of medical imaging data in relation to the novel image-to-image task to be performed by the downstream NN;

training the downstream NN by pretraining the downstream NN for reproducing the output of the subset of the layers of the set of pretext NN subsystems, wherein the training is further performed using a training database of medical imaging data in relation to the novel image-to-image task to be performed by the downstream NN; and applying the trained downstream NN to a current medical imaging data set received from a medical scanner.

4. The method according to claim 1, wherein the at least one predetermined transformation operation in the step of generating the set of transformed patches is selected from the group consisting of:

a rotation by a discrete angle, the discrete angle being an integer multiple of 90° along a symmetry axis of the cropped patch;

masking one or more voxels, and/or pixels, of the cropped patch with noise;

changing of an intensity of one or more voxels, and/or pixels, of the medical imaging data of the cropped patch;

inpainting on the cropped patch, wherein the inpainting comprises removing, and/or obfuscating, a region of the image, and/or of any one of the masks of the multi-mask, of the cropped patch;

shuffling subpatches of the cropped patch, wherein the shuffling comprises permuting spatial positions of the subpatches; and in case the medical imaging data comprise a temporal sequence of data, shuffling temporal instances of the cropped patch, wherein the shuffling of temporal instances comprises permuting temporal assignments of the temporal instances.

5. The method according to claim 1, wherein the novel image-to-image task of the downstream NN is selected from the group consisting of:

a segmentation of one or more predetermined anatomical structures comprised in a medical imaging data set received from a medical scanner; and a classification of one or more predetermined anatomical structures comprised in the medical imaging data set received from the medical scanner.

6. The method according to claim 1, wherein the training of the pretext NN subsystems uses self-supervised learning (SSL) and/or weakly supervised learning, wherein the weakly supervised learning comprises determining a pretext NN subsystem-specific loss function in related to a created mask.

7. The method according to claim 1, wherein the training of the downstream NN comprises supervised learning, wherein the supervised learning comprises using training data sets comprising medical imaging data with masks.

8. The method according to claim 1, wherein the set of pretext NN subsystems comprises at least one image-to-image task selected from the group consisting of:

a segmentation of one or more anatomical structures comprised in the cropped patch;

a classification of the one or more anatomical structures comprised in the cropped patch;

a masking of the one or more anatomical structures comprised in the cropped patch;

a denoising of the cropped patch;

a rotation classification, and/or rotation recovery, of the cropped patch;

a flip classification, and/or flip recovery, of the cropped patch; and a contrastive task, wherein the contrastive task comprises identifying a positive pair in case of overlapping patches, and/or a negative pair in case of non-overlapping patches.

9. The method according to claim 1, wherein a NN architecture of any one of the pretext NN subsystems, and/or the downstream NN, comprises at least one encoder, and/or at least one decoder.

10. The method according to claim 1, wherein the medical imaging data set comprises a two-dimensional (2D) image data set and/or a three-dimensional (3D) image data set.

11. The method according to claim 1, wherein the medical imaging data set of any augmented training data set in the database is received from a predetermined medical imaging modality, wherein the predetermined medical imaging modality is selected from the group consisting of:
computed tomography (CT);
magnetic resonance imaging (MRI);
ultrasound (US);
positron emission tomography (PET);
single photon emission computed tomography (SPECT); and/or
radiography.

12. The method according to claim 1, wherein one patch is cropped per augmented training data set per training epoch, or wherein two or more non-overlapping patches are cropped per augmented training data set per training epoch.

13. The method according to claim 1, wherein a NN architecture of any one of the pretext NN subsystems, and/or the downstream NN, comprises a convolutional U-net architecture, a transformer architecture, and/or a combination of a convolutional U-net and transformer architecture.

14. A computing device for pretraining a downstream neural network (NN) for a novel image-to-image task to be performed on medical imaging data received from a medical scanner, comprising:

a database generating module configured for generating a database of augmented training data sets based on at least one database of pre-existing training data sets, wherein the database generating module comprises:

a mask creating sub-module configured for creating a mask in relation to each of a set of existing trained image-to-image models by applying each existing trained image-to-image model within the set to a pre-existing training data set within the at least one database of pre-existing training data sets, wherein each existing trained image-to-image model within the set of existing trained image-to-image models is trained for creating a mask in relation to a medical imaging data set comprised in at least one of the pre-existing training data sets;

an aggregating sub-module configured for aggregating the created masks for the pre-existing training data set into a multi-mask; and an assembling sub-module configured for assembling the augmented training data set, wherein the augmented training data set comprises the aggregated multi-mask and the medical imaging data set from the pre-existing training data set;

a pretext task training module configured for training a set of pretext NN subsystems for performing pretext tasks using the generated database of augmented training data sets, wherein the set of pretext NN subsystems comprises at least two different pretext NN subsystems, wherein the pretext task training module comprises:

an augmented training data set selecting sub-module configured for selecting an augmented training data set from the generated database;

a patch cropping sub-module configured for cropping a patch from the selected augmented training data set, wherein the cropping comprises cropping the medical imaging data set and the aggregated multi-mask of the augmented training data set at the same voxel location and/or pixel location for the multi-mask and the medical imaging data set;

a transformed patches generating module configured for generating a set of transformed patches, wherein the generating of the set of transformed patches comprises performing at least one predetermined transformation operation on the cropped patch;

a set of pretext NN subsystems configured for performing the pretext tasks, wherein one or more generated transformed patches are used as input for each pretext NN subsystem, wherein any one, or each, pretext task comprises classifying, and/or applying an inverse of, the at least one predetermined transformation operation, wherein the training further comprises determining a pretext NN subsystem-specific loss function, wherein the pretext NN subsystem-specific loss function is indicative of a similarity of an output of the pretext NN subsystem and a mask within the aggregated multi-mask, and/or a similarity of the output of the pretext NN subsystem and medical imaging data, comprised in the cropped patch, wherein the at least two different pretext NN subsystems differ in a type of output, wherein the type of output comprises a mask according to one of the masks within the aggregated multi-mask, a classification of the at least one predetermined transformation operation, and/or a reconstructed version of the medical imaging data; and a pretext NN subsystem modifying sub-module configured for modifying each pretext NN subsystem within the set of pretext NN subsystems based on a predetermined combination of task-specific loss functions of the at least two different pretext NN subsystems, wherein the modifying comprises modifying one or more weights of the pretext NN subsystem; and a downstream NN pretraining module configured for pretraining the downstream NN for the novel image-to-image task to be performed on medical imaging data received from a medical scanner, wherein the pretraining is based on a subset of the one or more modified weights of the pretext NN subsystems, and/or based on an output of a subset of layers of the set of pretext NN subsystems.

15. The computing device according to claim 14, wherein the computing device is further configured to perform at least one of the steps of:

selecting the set of existing trained image-to-image models for the step of generating the database of augmented training data sets; and receiving, from the at least one database, the pre-existing training data sets for the step of generating the database of augmented training data sets.

16. A system for pretraining the downstream NN for the novel image-to-image task to be performed on the medical imaging data received from the medical scanner, comprising:

the computing device according to claim 14; and the downstream NN, which is configured for being pretrained by the downstream NN pretraining module of the computing device.

17. A non-transitory computer-readable medium on which program elements are stored that can be read and executed by a computing device for pretraining a downstream neural network (NN) for a novel image-to-image task to be performed on medical imaging data received from a medical scanner, the program elements, when executed by the computing device, carry out the steps of:

generating a database of augmented training data sets based on at least one database of pre-existing training data sets, wherein generating an augmented training data set for the database of augmented training data sets from an existing training data set comprises:

creating a mask in relation to each of a set of existing trained image-to-image models by applying each existing trained image-to-image model within the set to a pre-existing training data set within the at least one database of pre-existing training data sets, wherein each existing trained image-to-image model within the set of existing trained image-to-image models is trained for creating a mask in relation to a medical imaging data set comprised in at least one of the pre-existing training data sets;

aggregating the created masks for the pre-existing training data set into a multi-mask; and assembling the augmented training data set, wherein the augmented training data set comprises the aggregated multi-mask and the medical imaging data set from the pre-existing training data set;

training a set of pretext NN subsystems for performing pretext tasks using the generated database of augmented training data sets, wherein the set of pretext NN subsystems comprises at least two different pretext NN subsystems, wherein the training comprises:

selecting an augmented training data set from the generated database;

cropping a patch from the selected augmented training data set, wherein the cropping comprises cropping the medical imaging data set and the aggregated multi-mask of the augmented training data set at the same voxel location and/or pixel location for the multi-mask and the medical imaging data set;

generating a set of transformed patches, wherein the generating of the set of transformed patches comprises performing at least one predetermined transformation operation on the cropped patch;

performing the pretext tasks using the set of pretext NN subsystems, wherein one or more generated transformed patches are used as input for each pretext NN subsystem, wherein any one, or each, pretext task comprises classifying, and/or applying an inverse of, the at least one predetermined transformation operation, wherein the training further comprises determining a pretext NN subsystem-specific loss function, wherein the pretext NN subsystem-specific loss function is indicative of a similarity of an output of the pretext NN subsystem and a mask within the aggregated multi-mask, and/or a similarity of the output of the pretext NN subsystem and medical imaging data, comprised in the cropped patch, wherein the at least two different pretext NN subsystems differ in a type of output, wherein the type of output comprises a mask according to one of the masks within the aggregated multi-mask, a classification of the at least one predetermined transformation operation, and/or a reconstructed version of the medical imaging data; and modifying each pretext NN subsystem within the set of pretext NN subsystems based on a predetermined combination of task-specific loss functions of the at least two different pretext NN subsystems, wherein the modifying comprises modifying one or more weights of the pretext NN subsystem; and pretraining the downstream NN for the novel image-to-image task to be performed on medical imaging data received from a medical scanner, wherein the pretraining is based on a subset of the one or more modified weights of the pretext NN subsystems, and/or based on an output of a subset of layers of the set of pretext NN subsystems.

18. The non-transitory computer-readable medium according to claim 17, wherein the steps further comprise at least one of:

selecting the set of existing trained image-to-image models for the step of generating the database of augmented training data sets; and receiving, from the at least one database, the pre-existing training data sets for the step of generating the database of augmented training data sets.

19. The non-transitory computer-readable medium according to claim 17, wherein the steps further comprise at least one of:

training the downstream NN by initializing weights of the downstream NN based on the subset of the modified weights of the pretext NN subsystems, wherein the training is performed using a training database of medical imaging data in relation to the novel image-to-image task to be performed by the downstream NN;

training the downstream NN by pretraining the downstream NN for reproducing the output of the subset of the layers of the set of pretext NN subsystems, wherein the training is further performed using a training database of medical imaging data in relation to the novel image-to-image task to be performed by the downstream NN; and applying the trained downstream NN to a current medical imaging data set received from a medical scanner.

20. The non-transitory computer-readable medium according to claim 17, wherein the at least one predetermined transformation operation in the step of generating the set of transformed patches is selected from the group consisting of:

a rotation by a discrete angle, the discrete angle being an integer multiple of 90° along a symmetry axis of the cropped patch;

masking one or more voxels, and/or pixels, of the cropped patch with noise;

changing of an intensity of one or more voxels, and/or pixels, of the medical imaging data of the cropped patch;

inpainting on the cropped patch, wherein the inpainting comprises removing, and/or obfuscating, a region of the image, and/or of any one of the masks of the multi-mask, of the cropped patch;

shuffling subpatches of the cropped patch, wherein the shuffling comprises permuting spatial positions of the subpatches; and in case the medical imaging data comprise a temporal sequence of data, shuffling temporal instances of the cropped patch, wherein the shuffling of temporal instances comprises permuting temporal assignments of the temporal instances.

* * * * *